(12) United States Patent
Dakka et al.

(10) Patent No.: US 8,771,815 B2
(45) Date of Patent: Jul. 8, 2014

(54) PROCESS FOR MAKING TRIGLYCERIDE PLASTICIZER

(75) Inventors: Jihad Mohammed Dakka, Whitehouse Station, NJ (US); Edmund John Mozeleski, Califon, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 486 days.

(21) Appl. No.: 12/971,629

(22) Filed: Dec. 17, 2010

(65) Prior Publication Data

US 2011/0151162 A1 Jun. 23, 2011

Related U.S. Application Data

(63) Continuation-in-part of application No. 12/653,744, filed on Dec. 17, 2009.

(51) Int. Cl.
*C08K 5/103* (2006.01)
*C08K 5/101* (2006.01)

(52) U.S. Cl.
USPC .......... 428/35.7; 524/312; 524/287; 524/306; 524/311; 524/313

(58) Field of Classification Search
USPC .................. 524/312, 287, 306; 560/190, 191; 428/35.7
See application file for complete search history.

(56) References Cited

U.S. PATENT DOCUMENTS

| | | |
|---|---|---|
| 4,273,936 A | 6/1981 | Fiato et al. |
| 5,137,952 A | 8/1992 | Miller et al. |
| 5,248,531 A | 9/1993 | Nagai et al. |
| 5,877,358 A | 3/1999 | Garton et al. |
| 6,013,851 A | 1/2000 | Verrelst et al. |

(Continued)

FOREIGN PATENT DOCUMENTS

| | | |
|---|---|---|
| WO | 9932427 | 7/1999 |
| WO | 0015190 | 3/2000 |

(Continued)

OTHER PUBLICATIONS

Godwin, A.D., "Plasticizers", Applied Polymer Science 21st Century, edited by C.D. Craver and C. E. Carraher, Elsevier (2000), pp. 157-175.

(Continued)

*Primary Examiner* — Ellen S Raudenbush
(74) *Attorney, Agent, or Firm* — Robert A. Migliorini

(57) ABSTRACT

Provided are processes for making, and processes for using triglycerides as plasticizers. The process for making the triglyceride plasticizer includes: (i) recovering at least one linear $C_4$ to $C_{10}$ aldehyde, one branched $C_4$ to $C_{10}$ aldehyde, or a combination thereof from a hydroformylation product; (ii) oxidizing the linear, branched or combination thereof $C_4$ to $C_{10}$ aldehyde to form a linear, branched or combination thereof $C_4$ to $C_{10}$ acid; (iii) esterifying the linear, branched or combination thereof $C_4$ to $C_{10}$ acid with a polyol to yield a linear alkyl triglyceride, a branched alkyl triglyceride, or a combination thereof, and reaction byproducts; (iv) purifying the linear, branched or combination thereof alkyl triglyceride to form a plasticizer stream, a reaction byproduct stream, and an unreacted input stream, wherein the total carbon number of the triester groups ranges from 20 to 25 for greater than or equal to 45 wt % of the plasticizer; and (v) recycling from the purifying step back to the esterifying step the unreacted input stream and the reaction byproduct stream.

69 Claims, 7 Drawing Sheets

(56) References Cited

U.S. PATENT DOCUMENTS

| | | | |
|---|---|---|---|
| 6,652,774 B2 * | 11/2003 | Zhou et al. | 252/182.24 |
| 6,734,241 B1 | 5/2004 | Nielsen et al. | |
| 6,740,254 B2 | 5/2004 | Zhou et al. | |
| 6,811,722 B2 | 11/2004 | Zhou et al. | |
| 6,969,735 B1 | 11/2005 | Godwin et al. | |
| 6,969,736 B1 | 11/2005 | Godwin et al. | |
| 6,982,295 B2 | 1/2006 | Godwin et al. | |
| 7,081,553 B2 | 7/2006 | Clausi et al. | |
| 7,081,554 B2 | 7/2006 | Garton et al. | |
| 7,145,049 B2 | 12/2006 | Loescher et al. | |
| 7,148,388 B2 | 12/2006 | Beadle et al. | |
| 7,186,874 B2 | 3/2007 | Dakka et al. | |
| 7,297,738 B2 | 11/2007 | Gosse et al. | |
| 7,345,212 B2 | 3/2008 | Beadle et al. | |
| 8,163,825 B2 * | 4/2012 | Colle et al. | 524/312 |
| 2004/0242948 A1 | 12/2004 | Mathys et al. | |
| 2005/0020718 A1 * | 1/2005 | Gosse et al. | 523/105 |
| 2006/0247461 A1 | 11/2006 | Schlosberg et al. | |
| 2009/0149585 A1 * | 6/2009 | De Quadros Junior et al. | 524/114 |

FOREIGN PATENT DOCUMENTS

| | | |
|---|---|---|
| WO | 03029339 | 4/2003 |
| WO | 03050070 | 6/2003 |
| WO | 2004046078 | 6/2004 |
| WO | 2006055106 | 5/2006 |
| WO | 2006086067 | 8/2006 |
| WO | 2007040812 | 4/2007 |
| WO | 2007106215 | 9/2007 |

OTHER PUBLICATIONS

Shoba, H.K. and Kishore, K., Structural Expressions of Long-Chain Esters on Their Plasticizing Behavior in Poly (vinyl chloride), Macromolecules, 1992, 25, pp. 6765-6769.

Riser, G.R. and Palm, W.E., "A Method of Determining Compatibility Parameters of Plasticizers for Use in PVC Through Use of Torsional Modulus", Polymer Engineering and Science, Apr. 1967, pp. 110-114.

Periodic Table, Chemical Engineering News, 63(5), 27 (1985).

Sears, J. and Darbey, J., "The Technology of Plasticizers", John Wiley & Sons, New York, 1982, pp. 95-99.

Small, P.A., "Some Factors Affecting the Solubility of Polymers", J. Appl. Chem., 3, pp. 76-80 (1953).

* cited by examiner

PROCESS FOR MAKING TRIGLYCERIDE PLASTICIZER

CROSS-REFERENCE TO RELATED APPLICATIONS

This application is a Continuation-in-Part of and claims priority to U.S. patent application Ser. No. 12/653,744, filed on Dec. 17, 2009 and incorporated by reference herein in its entirety.

FIELD

The present disclosure relates to processes for making triglycerides based on linear or branched alkyl groups, useful as plasticizers and viscosity depressants for a wide range of polymer resins.

BACKGROUND

Plasticizers are incorporated into a resin (usually a plastic or elastomer) to increase the flexibility, workability, or distensibility of the resin. The largest use of plasticizers is in the production of "plasticized" or flexible polyvinyl chloride (PVC) products. Typical uses of plasticized PVC include films, sheets, tubing, coated fabrics, wire and cable insulation and jacketing, toys, flooring materials such as vinyl sheet flooring or vinyl floor tiles, adhesives, sealants, inks, and medical products such as blood bags and tubing, and the like.

Other polymer systems that use small amounts of plasticizers include polyvinyl butyral, acrylic polymers, poly(vinylidene chloride), nylon, polyolefins, polyurethanes, and certain fluoroplastics. Plasticizers can also be used with rubber (although often these materials fall under the definition of extenders for rubber rather than plasticizers). A listing of the major plasticizers and their compatibilities with different polymer systems is provided in "Plasticizers," A. D. Godwin, in Applied Polymer Science 21st Century, edited by C. D. Craver and C. E. Carraher, Elsevier (2000); pp. 157-175.

Plasticizers can be characterized on the basis of their chemical structure. The most important chemical class of plasticizers is phthalic acid esters, which accounted for about 85% worldwide of PVC plasticizer usage in 2002. However, in the recent past there as been an effort to decrease the use of phthalate esters as plasticizers in PVC, particularly in end uses where the product contacts food, such as bottle cap liners and sealants, medical and food films, or for medical examination gloves, blood bags, and IV delivery systems, flexible tubing, or for toys, and the like. For these and most other uses of plasticized polymer systems, however, a successful substitute for phthalate esters has heretofore not materialized.

One such suggested substitute for phthalates are esters based on cyclohexanoic acid. In the late 1990's and early 2000's, various compositions based on cyclohexanoate, cyclohexanedioates, and cyclohexanepolyoate esters were said to be useful for a range of goods from semi-rigid to highly flexible materials. See, for instance, WO 99/32427, WO 2004/046078, WO 2003/029339, WO 2004/046078, U.S. Application No. 2006-0247461, and U.S. Pat. No. 7,297,738.

Other suggested substitutes include esters based on benzoic acid (see, for instance, U.S. Pat. No. 6,740,254, and also co-pending, commonly-assigned, U.S. Patent Application 61/040,480 and polyketones, such as described in U.S. Pat. No. 6,777,514; and also co-pending, commonly-assigned, U.S. application Ser. No. 12/058,397. Epoxidized soybean oil, which has much longer alkyl groups ($C_{16}$ to $C_{18}$) has been tried as a plasticizer, but is generally used as a PVC stabilizer. Stabilizers are used in much lower concentrations than plasticizers.

Typically, the best that has been achieved with substitution of the phthalate ester with an alternative material is a flexible PVC article having either reduced performance or poorer processability. Thus, heretofore efforts to make phthalate-free plasticizer systems for PVC have not proven to be entirely satisfactory, and this is still an area of intense research.

Plasticizers based on triglycerides have been tried in the past, but they have mostly been based on natural triglycerides from various vegetable oils. The alkyl groups on these natural triglycerides are linear, and can cause compatibility problems when the alkyl chain is too long.

"Structural Expressions of Long-Chain Esters on Their Plasticizing Behavior in Poly(vinyl Chloride)", H. K. Shobha and K. Kishore, Macromolecules 1992, 25, 6765-6769, reported the influence of branching and molecular weight in long-chain esters in PVC. Triglycerides (TGE's) having linear alkyl groups were studied.

"A Method for Determining Compatibility Parameters of Plasticizers for Use in PVC Through Use of Torsional Modulus", G. R. Riser and W. E. Palm, Polymer Engineering and Science, April 1967, 110-114, also investigate the use of triglycerides and their plasticizing behavior with PVC, including tri-iso-valerin (3-methyl butanoate)triglyceride. It was reported that "these materials have volatilities that are much too high for good long-time permanence".

Nagai et al. in U.S. Pat. No. 5,248,531, teaches the use of articles comprising vinyl chloride-type resins (among others) using triglyceride compounds as a hemolysis depressant, and also comprising 10 to 45 wt % of plasticizers selected from trialkyl trimellitates, di-normal alkyl phthalates, and tetraalkyl pyromellitates. The alkyl chains of the acid-derived moiety $R^1$-$R^3$ in the structure below, formula (I), are independently an aliphatic hydrocarbon group of one to 20 carbon atoms and in embodiments at least one of the alkyl chains is branched. One specific triglyceride disclosed is glyceryl tri-2-ethylhexanoate.

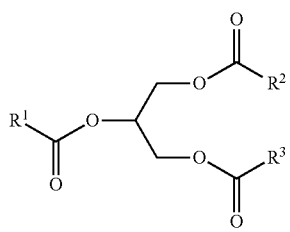

I

Zhou et al. discloses, in U.S. Pat. Nos. 6,652,774; 6,740,254; and 6,811,722; phthalate-free plasticizers comprising a mixture of different triesters of glycerin, preferably wherein the phthalate-free plasticizer is formed by a process of esterifying glycerin with a mixture comprising a mixture of alkyl acids and aryl acids. Zhou et al. also discloses that glyceryl tribenzoate and glyceryl tri(2-ethyl)hexanoate have not been used as primary plasticizers in vinyl polymers, such as PVC because they are known to be incompatible with such resins.

Nielsen et al., in U.S. Pat. No. 6,734,241, teach a composition comprising a thermoplastic polymer as in formula (I) above, wherein at least one of the R groups is an alkyl group having from one to five carbon atoms and at least one of the R groups is a saturated branched alkyl group having from 9 to 19 carbon atoms and a hydrophilic group.

Among the problems presented by the aforementioned triglycerides is they cannot be made conveniently and thus generally are quite expensive and/or are specialty chemicals not suitable as replacements for phthalates from an economic standpoint and/or are not as compatible with the range of polymer systems that phthalates are compatible with, and thus are not viable replacements for phthalates from a physical property standpoint.

For instance, some synthesis methods involve at least two separate steps, such as where the glycerol is first partially esterified with the $C_{10}$ to $C_{20}$ branched chain acyl group and then reacted with acetic acid or acetic anhydride.

Other syntheses involving mixed acid feeds will require addition of a hydrocarbon solvent for azeotropic distillation of the water to drive the esterification reaction to completion (as measured by the hydroxyl number of the ester, which is a measure of the amount of unreacted OH groups), due to the spread in boiling points between the mixed acids. In addition, the use of mixed acid feedstock such as cited in Zhou et al. and in Nielsen et al. can reduce the capability of recycling unreacted acids.

Triglycerides based on acids derived from natural products will be limited to naturally occurring linear alkyl groups with even carbon numbers, which offer very little flexibility in designing an appropriate plasticizer system for a given polymer system.

Thus what is needed is a method of making a general purpose non-phthalate plasticizer having high throughput and providing a plasticizer having a suitable melting or glass transition or pour point, increased compatibility, good performance and low temperature properties.

The present inventors have surprisingly discovered an improved process that yields triglycerides with a total carbon number of the triester groups between 20 and 25 (not including the three glycerol backbone carbons), produced by esterification of glycerol with a combination of acids derived from the hydroformylation and subsequent oxidation of $C_3$ to $C_9$ olefins, provide for triglycerides for excellent compatibility with a wide variety of resins and that can be made with a high throughput. Esterification of glycerol using a combination of acids eliminates many of the aforementioned problems, and enables high yield of the glycerol triesters to be obtained, having excellent compatibility with vinyl polymers.

SUMMARY

The present disclosure is directed to a process for producing a plasticizer including: (i) recovering at least one linear $C_4$ to $C_{10}$ aldehyde, one branched $C_4$ to $C_{10}$ aldehyde, or a combination thereof from a hydroformylation product; (ii) oxidizing the linear, branched or combination thereof $C_4$ to $C_{10}$ aldehyde to form a linear, branched or combination thereof $C_4$ to $C_{10}$ acid; (iii) esterifying the linear, branched or combination thereof $C_4$ to $C_{10}$ acid with a polyol to yield a linear alkyl triglyceride, a branched alkyl triglyceride, or a combination thereof, and reaction byproducts; (iv) purifying the linear, branched or combination thereof alkyl triglyceride to form a plasticizer stream, a reaction byproduct stream, and an unreacted input stream, wherein the total carbon number of the triester groups ranges from 20 to 25 for greater than or equal to 45 wt % of the plasticizer; and (v) recycling from the purifying step back to the esterifying step the unreacted input stream and the reaction byproduct stream.

The present disclosure is also directed to a process for producing a plasticizer including: (i) recovering an aldehyde/alcohol mixture including at least one linear $C_4$ to $C_{10}$ aldehyde, one branched $C_4$ to $C_{10}$ aldehyde, or a combination thereof and at least one linear $C_4$ to $C_{10}$ alcohol, one branched $C_4$ to $C_{10}$ alcohol, or a combination thereof from a hydroformylation process; (ii) oxidizing the aldehyde/alcohol mixture to form a linear, branched or combination thereof $C_4$ to $C_{10}$ acid; (iii) esterifying the linear, branched or combination thereof $C_4$ to $C_{10}$ acid with a polyol to yield a linear alkyl triglyceride, a branched alkyl triglyceride, or a combination thereof, and reaction byproducts; (iv) purifying the linear, branched or combination thereof alkyl triglyceride to form a plasticizer stream, a reaction byproduct stream and an unreacted input stream, wherein the total carbon number of the triester groups ranges from 20 to 25 for greater than or equal to 45 wt % of the plasticizer; and (v) recycling from the purifying step back to the esterifying step the unreacted input stream and the reaction byproduct stream.

These and other objects, features, and advantages will become apparent as reference is made to the following detailed description, embodiments, examples, and appended claims.

BRIEF DESCRIPTION OF THE DRAWINGS

In the accompanying drawings, like reference numerals are used to denote like parts throughout the several views.

DETAILED DESCRIPTION

Figure 1:
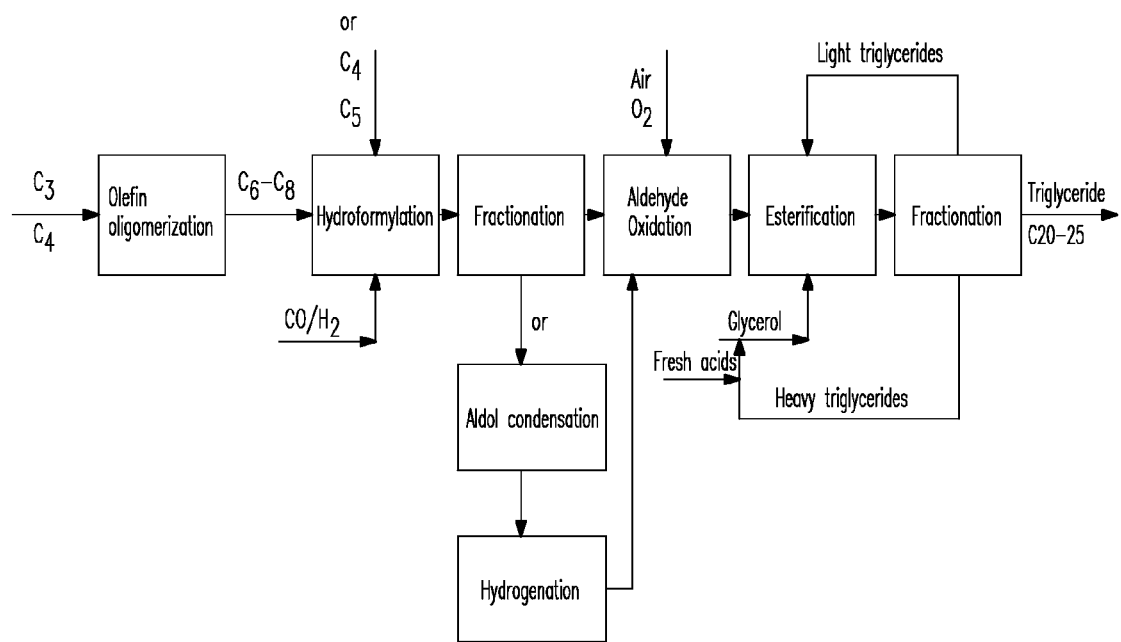
FIG. 1 is a schematic representation of a process according to a preferred embodiment of the invention.

The present disclosure provides triglycerides and methods of making triglycerides for use as plasticizers for polymer resins. In one form of the present disclosure, the triglyceride plasticizer is "phthalate-free". As used in the instant specification and in the appended claims, the term "phthalate-free" means that the plasticizer does not contain any phthalate diesters, which are also known in the art simply as phthalates.

Referring to the triglyceride chemical formula below, for the instant application including the claims, the total carbon number of the triester groups is defined as the sum of the carbons for the $R^1$, $R^2$ and $R^3$ groups plus the three carbons for the three carbonyl groups, and not including the three glycerol backbone carbons. Hence for illustrative purposes, for a $C_8$ triglyceride (also referred to as 888 triglyceride), the total carbon number would be 24 as defined herein (7+7+7=21 carbons from the $R^1$, $R^2$, and $R^3$ alkyl groups plus three carbonyl group carbons) because the three glycerol backbone carbons are not included in the calculation. For a $C_7$ triglyceride (also referred to as 777 triglyceride), the total carbon number would be 21 as defined herein (6+6+6=18 carbons from the $R^1$, $R^2$, and $R^3$ alkyl groups plus three carbonyl group carbons) because the three glycerol backbone carbons again are not included in the calculation.

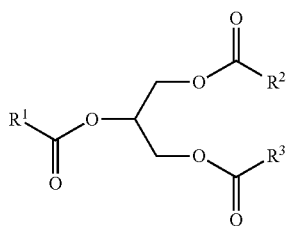

According to the present disclosure, the triglycerides disclosed herein may be produced by esterification of one or more $C_4$ to $C_{10}$ linear or branched acids with glycerol to form a triglyceride with a total carbon number of the linear or branched alkyl triester groups ranging from 20 to 25 (including the three carbons for the three carbonyl groups and not including the three glycerol backbone carbons).

In one embodiment, the at least one or more $C_4$ to $C_{10}$ linear or branched acids will be derived from the hydroformylation of light olefins, aldol condensation of the light aldehydes and then hydrogenation followed by oxidation thus may be referred to herein as "oxo acids". The OXO Process is per se well known. By way of recent examples, see, for instance, U.S. Pat. Nos. 7,345,212; 7,186,874; 7,148,388; 7,081,554; 7,081,553; 6,982,295; 6,969,736; 6,969,735; 6,013,851; 5,877,358; and PCT publications WO 2007106215; WO 2007040812; WO 2006086067; WO 2006055106; WO 2003050070; WO 2000015190. As mentioned above, or alternatively directly oxidized to the desired acid(s). However, it will be recognized by one of skill in the art that the $C_4$ to $C_{10}$ linear or branched acids may be derived from other processes.

The present disclosure is also directed to the product of the process, which comprises at least one compound according to the following structure (I):

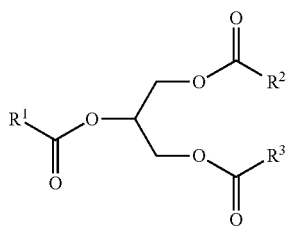

wherein the sum of the carbons for the linear or branched alkyl triester groups ($R^1$, $R^2$, and $R^3$ plus three carbons for the three carbonyl groups and not including the three glycerol backbone carbons) may range from 20 to 25. Alternatively, the sum of the carbons for the linear or branched alkyl triester groups ($R^1$, $R^2$, and $R^3$ plus three carbons for the three carbonyl groups and not including the three glycerol backbone carbons) may range from 20 to 24, or 20 to 23, or 20 to 22, or 20 to 21, or 22 to 25, or 23 to 25, or 24 to 25. In another form, the sum of the carbons for the $R^1$, $R^2$, and $R^3$ plus three carbons for the three carbonyl groups and not including the three glycerol backbone carbons may be 20, or 21, or 22, or 23, or 24, or 25.

The present disclosure is also directed to the product of the process, which comprises at least one compound according to structure (I), wherein the sum of the carbons for the branched alkyl triester groups ($R^1$, $R^2$, and $R^3$ plus three carbons for the three carbonyl groups and not including the three glycerol backbone carbons) may range from 20 to 25, and also wherein $R^1$, $R^2$, and $R^3$ are independently selected from $C_3$ to $C_9$ alkyl groups having an average branching of from about 0.8 to 3.0 branches per group or from about 0.8 to about 2.2 branches per group. Average branching is determined by Nuclear Magnetic Resonance (NMR) spectroscopy. In another form of this embodiment, the average branching may range from about 0.8 to about 1.8 branches per group. In yet another form, the average branching of the $C_3$ to $C_9$ branched alkyl groups ranges from about 0.8 to about 3.0, or from about 0.8 to about 1.6, or from about 1.2 to about 1.4 branches per group. The average branching of the sidechain groups will be a function of the average branching of the precursor OXO acids used in the esterification process. The average branching per triglyceride of structure (I) will equal three times the average branching per group, since each triglyceride bears three alkyl groups.

NMR analyses of the branching found in the OXO acids finds that these branches are typically methyl groups. For example, with the branched $C_7$ OXO acid, typical isomers include 3-methylhexanoic acid, 4-methylhexanoic acid, 5-methylhexanoic acid, as well as some 3,4-dimethylpentanoic acid, 2,4-dimethylpentanoic acid and 2,3-dimethylpentanoic acid. Some n-heptanoic acid is also present. Similar products are found with mixtures of isomers in the $C_8$ and $C_9$ OXO acids. $C_9$ OXO acids when prepared from the OXO reaction using diisobutylene as the olefin feed will give mostly trimethyl branched acids, such a 3,5,5-trimethylhexanoic acid. The OXO acids generally provide more than one isomer.

In the first step of the process for producing triglycerides disclosed herein, linear or branched aldehydes may be produced by hydroformylation of $C_3$ to $C_9$ olefins that in turn have been produced by propylene, butene, and/or pentene oligomerization over solid phosphoric acid or zeolite catalysts. The oligomerization processes are per se well-known. See, for instance, U.S. Pat. Nos. 7,253,330, and 7,145,049. The hydroformylation process step is depicted in FIG. 1. The hydroformylation process produces a mixture of aldehydes and alcohols depending upon the catalyst used and the processing conditions. In one form, the hydroformylation reaction may be catalyzed by a metal selected from Groups 8-10 according to the new notation for the Periodic Table as set forth in Chemical Engineering News, 63(5), 27 (1985). In particular, Ru catalysts tend to be more selective toward forming aldehydes as opposed to alcohols compared to Co catalysts. The non-limiting exemplary metal catalysts selected from Rh and Co may also be used with an organic ligand to further improve catalyst activity and selectivity. In another form, the feed for the hydroformylation process may be formed by dimerizing a feedstock selected from propylene, butenes, pentenes and mixtures thereof by solid phosphoric acid or a zeolite dimerization.

In one form, the resulting $C_4$ to $C_{10}$ aldehydes can then be recovered from the crude hydroformylation product stream by fractionation as depicted in FIG. 1 to remove unreacted olefins and the corresponding alcohols. These $C_4$ to $C_{10}$ aldehydes can then in turn be oxidized to their respective $C_4$ to $C_{10}$ acids using air or enriched air as an oxygen source as depicted in FIG. 1. In an alternative form, that avoids the previous fractionation step, the one or more $C_4$ to $C_{10}$ linear or branched alkyl aldehydes/alcohols can be oxidized to the corresponding acids and alcohols and then the unreacted aldehydes purified by distillation. The separated unreacted aldehydes plus the alcohols are oxidized to their corresponding acids. This alternative form may be particularly suitable when using a Ru catalyst during the hydroformylation process. In either of the preceding forms, the distilled aldehydes may be oxidized to an acid followed by fractionation to remove unreacted alcohol. The oxidizing steps may be either catalyzed or non-catalyzed.

Non-limiting exemplary acids include acetic acid, bromoacetic acid, propanoic acid, 2-chloropropanoic acid, 3-chloropropanoic acid, 2-methylpropanoic acid, 2-ethylpropanoic acid, 2-methylbutanoic acid, 3-methylbutanoic acid, 2-ethylbutanoic acid, 2,2-dimethylbutanoic acid, 2,3-dimethylbutanoic acid, 3,3-dimethylbutanoic acid, 2-methylpentanoic acid, 3-methylpentanoic acid, 4-methylpentanoic acid, cyclopentyl acetic acid, cyclopentyl propanoic acid, cyclopentyl hexanoic acid, cyclohexane carboxylic acid, cyclohexane acetic acid, 2-ethylhexanoic acid, nonadecafluorodecanoic acid, decanoic acid, and undecanoic acid.

Following the oxidation reaction, the $C_4$ to $C_{10}$ acids can then be purified by fractionation to remove unreacted aldehydes, lights and heavies formed during oxidation. Hence the instant process may utilize OXO acids, linear or branched acids, neo-acids, benzoic acid, toluic acid and combinations thereof. Commonly owned co-pending U.S. Ser. No. 12/880, 586, herein incorporated by reference in its entirety, discloses the use of neo acids for producing neoalkylester plasticizers. Commonly owned co-pending U.S. Ser. No. 12/878,166, herein incorporated by reference in its entirety, discloses the use of benzoic and toluic acids for producing mixed triglyceride plasticizers.

The $C_4$ to $C_{10}$ acids can then be esterified as depicted in FIG. 1 with glycerol or other alcohols including ethylene glycol, and other polyols. The esterification step may be catalyzed by at least one metal selected from Ti, Zr or Sn, or a mixture thereof, or catalyzed by an organic acid. In an alternative form, the esterification step may be uncatalyzed. The esterification step may occur at a temperature ranging from 120 to 250° C., or 150 to 220° C., or 170 to 200° C. The esterification step may occur at a pressure ranging from 100 mm Hg to 760 mm Hg, or 200 mm Hg to 660 mm Hg, or 300 to 500 mm Hg. The esterification step may occur at a reaction time of 1 hour to 24 hours, or 5 hours to 20 hours, or 10 hours to 15 hours. The esterification step may occur at a reactor residence time of 1 to 100 minutes, or 10 to 90 minutes, or 20 to 80 minutes, or 40 to 70 minutes.

Single carbon number linear or branched acids can be used in the esterification, or linear or branched acids of differing carbon numbers can be use to optimize product cost and performance requirements. Hence, a combination of one or more linear or branched $C_4$ to $C_{10}$ acids may be esterified to form mixed triglycerides including linear or branched alkyl esters, wherein the total carbons for the triester groups ($R^1$, $R^2$, and $R^3$ plus three carbons for the three carbonyl groups and not including the three glycerol backbone carbons) ranges from 20 to 25. Such range of total carbons for the triester groups yield triglycerides with outstanding performance when used as plasticizers for polymeric resins. More particularly, triglycerides with linear or branched alkyl groups and a total carbon number of the triester groups ranging from 20 to 25 have been discovered to yield low volatility and excellent compatibility with a broad range of polymeric resins, including PVC. Such triglycerides also yield outstanding low temperature performance properties.

Glycerol is currently an attractive polyol for use to make plasticizers because it is abundantly available. It is, for instance, a major byproduct of biodiesel production. Other polyols, however, may be utilized to produce plasticizers, such as glycols, preferably ethylene glycol or propylene glycol. Mixtures of polyols may be used, such as a mixture of glycerol with propylene glycol.

It is preferred that the polyols be fully esterified so that there are a low to negligible amount of free hydroxyl groups. Thus, for example, it is preferred that glycerol is esterified to the triester.

Following the esterification process, a fractionation process, such as distillation, may be used to separate the $C_{20}$ to $C_{25}$ triglycerides from the lighter and heavier triglycerides. The light triglycerides may be recycled back to the esterification step of the process. The heavy triglycerides may also be recycled back to the esterification step of the process after adding fresh acids and polyol. The $C_{20}$ to $C_{25}$ triglyceride may be chosen from 669 triglyceride, 696 triglyceride, 699 triglyceride, 969 triglyceride, 5510 triglyceride, 5105 triglyceride, 51010 triglyceride, 10510 triglyceride, 677 triglyceride, 767 triglyceride, and 777 triglyceride. Note however that these $C_{20}$ to $C_{25}$ triglycerides may include other proportions (55 wt % or less relative to the total) of triglycerides which do not have a total carbon number of the triester groups falling within the 20 to 25 range. If the total weight % of these non-inventive triglycerides is greater than 55 wt %, plasticizer properties (volatility, compatibility, low temperature performance, etc.) will begin to be negatively impacted. Hence, for the $C_{20}$ to $C_{25}$ triglycerides disclosed herein, linear or branched alkyl triglycerides with a total carbon number of from 20 to 25 should comprise greater than or equal to 45 wt %, or greater than or equal to 60 wt %, or greater than or equal to 75 wt %, or greater than or equal to 90 wt %, or greater than or equal to 95 wt %, or greater than or equal to 97 wt %, or greater than or equal to 99 wt %, or greater than or equal to 99.5 wt %, or greater than or equal to 99.9 wt % of the plasticizer. The fractionation process following the esterification step may be used to increase the purity of $C_{20}$ to $C_{25}$ triglycerides.

Figure 6:
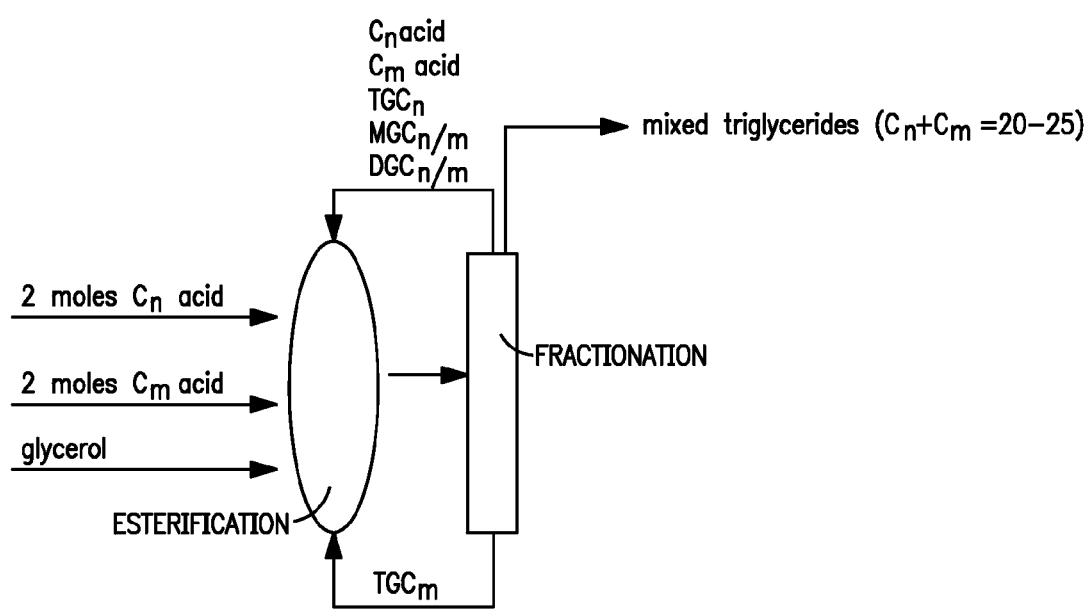
FIG. 6 is a process schematic of the improved esterification and fractionation process with recycle of the current disclosure.

The esterification and fractionation processes of FIG. 1 are depicted in greater detail in FIG. 6. As FIG. 6 depicts, a slip stream from the esterification reactor is continuously removed and provided to a distillation column (fractionation step), wherein the unreacted acid, light triglyceride, heavy triglyceride are recycled back to the esterification reactor for doing esterification and transesterification, and triglycerides having a carbon number of $C_{20}$ to $C_{25}$ are removed as the process product. In addition, in one form of the process discussed below, monoglycerides and diglycerides are also fractionated and recycled back to the esterification reactor. By running the esterification reaction at partial conversion (90%) to maximize the reaction efficiency and using fractionation in which unreacted acids, monoglyceride (MGC), diglyceride (DGC) and heavy and light triglyceride (TGC) are recycled to the esterification reaction for transesterification to obtain an equilibrium mixture.

In one advantageous form of FIG. 6, the ratio of alcohol groups to acid groups in the esterification process is in the range of 1 alcohol to 1.1 acid groups to 1 alcohol group to 10 acid groups. In other forms, the ratio of alcohol to acid groups in the esterification process may be from 1 to 9, or 1 to 7, or 1 to 5, or 1 to 3, or 1 to 2, or 1 to 1.5. Hence, in this advantageous form of the disclosed process, there is an excess of acid groups to alcohol groups. In the inventive process disclosed herein, the excess acid groups (Cm acid and Cn acid in FIG. 6) are separated in the fractionation step and recycled back to the esterification process. In addition to the unreacted acid (Cm acid and Cn acid) from the fractionation process being recycled back to the esterification process, light triglycerides (less than $C_{20}$) and heavy triglycerides (greater than $C_{25}$) are also separated out in the fractionation process and recycled back to the esterification reactor. The output of the fractionation process is mixed triglycerides falling within the $C_{20}$ to $C_{25}$ triglycerides range. By running the esterification reaction with an excess of acid with respect to alcohol, and recycling the unreacted acid and heavy and light triglyceride back to the esterification reactor, an equilibrium mixture is achieved in the esterification reactor and 100% conversion of the alcohol is also achieved.

Figure 7:
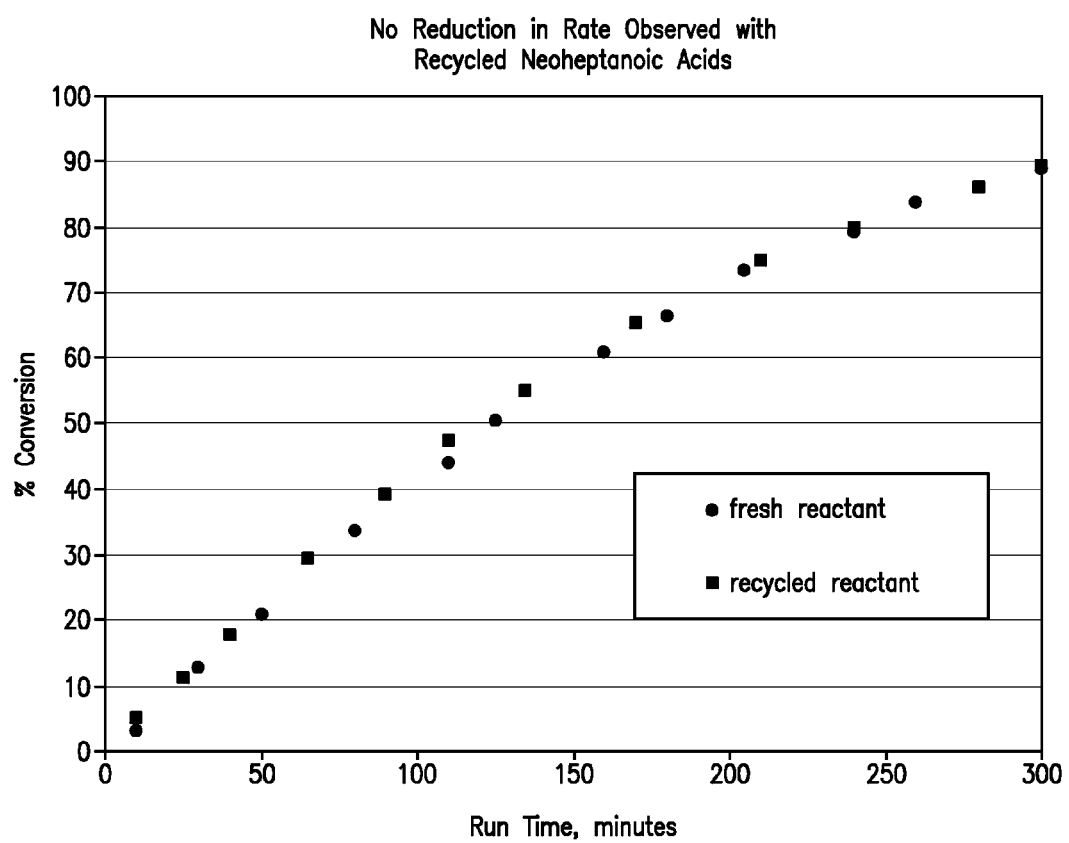
FIG. 7 is a graph of percent conversion of alcohol versus reaction time with fresh acid and recycled acid.

Unexpectedly, the applicants have discovered that the use of recycled acid in comparison to fresh acid does not slow down the esterification reaction rate, which indicates that isomerization of the acid does not change the esterification reaction. That is the reaction rate of the esterifying step with only fresh acid $C_4$ to $C_{10}$ acid feed is substantially similar to the reaction rate when recycled $C_4$ to $C_{10}$ acid is also used in the esterifying step. By "substantially similar", the applicants mean that there is less than a 5%, or less than a 3%, or less than a 1% decrease in the reaction rate during the esterification reaction upon the use of recycled $C_4$ to $C_{10}$ acid back into the esterifying step compared to when only fresh $C_4$ to $C_{10}$ acid is used in the esterifying step. Hence, the use of recycled unreacted $C_4$ to $C_{10}$ acid does not negatively impact the reaction rate of the esterifying step compared to when only fresh $C_4$ to $C_{10}$ acid is used in the esterifying step. Support for this discovery may be found in FIG. 7. Referring to FIG. 7, the triglyceride reaction rate with neoheptanoic acids as measured by % conversion of reactant (glycerol+either fresh acid or recycled acid) versus reaction run time is essentially the same whether fresh reactant (fresh acid and fresh glycerol) or recycled reactant (recycled acid and fresh glycerol) is used. Fresh acid and recycled acid yield the same reaction rate in the esterification reactor, and hence the isomer distribution of the fresh acid is the same or similar to that of the recycled acid. The esterification reaction is not selective to any isomers. The transesterification rate is surprisingly not impacted when an excess of acid is used in the esterification reactor, and the excess acid is recycled back to the esterification reactor.

In this form of the esterification and fractionation process shown in FIGS. 1 and 6, the applicants have discovered there is an improved yield of $C_{20}$ to $C_{25}$ triglycerides when excess acid relative to alcohol (also referred to as "non-stoichiometric with excess acid form") is used in the transesterification step (esterification reactor). In this form, monoglycerides (MGC) and diglycerides (DGC) formed in the esterification step are minimal, and hence there no need to recycle them back to the esterification reactor.

In an alternative form of the esterification and fractionation process shown in FIGS. 1 and 6, a stoichiometric amount of acid to alcohol is used in the esterification reactor (also referred to as "stoichiometric with no excess acid form"). In this form, the esterification reaction yields not only triglycerides, but also monoglycerides and diglycerides. The monoglycerides (MGC), diglycerides (DGC), light triglycerides (less than $C_{20}$) and heavy triglycerides (greater than $C_{25}$) are separated from the $C_{20}$ to $C_{25}$ triglycerides in the fractionation process and recycled back to the esterification reactor. In this form, the esterification process will also reach an equilibrium condition, however it is less advantageous with respect to the "non-stoichiometric with excess acid form" discussed above because the monoglycerides and diglycerides recycled back to the esterification process may form olefins, aldehydes, ketones, ethers and combinations thereof which results in a lower yield of triglycerides formed. Also in this "stoichiometric with no excess acid form", there is not 100% conversion of the alcohol as in the "non-stoichiometric with excess acid form" discussed above. However, in the "stoichiometric with no excess acid form", there is no excessive unreacted acid from the esterification reactor, and hence no need to recycle any excess acid from the downstream fractionation step to the esterification reactor.

In yet another form of the esterification and fractionation process shown in FIGS. 1 and 6, there may be an excess of alcohol groups to acids group. That is, the ratio of alcohol groups to acid groups in the esterification process is in the range of 1.1 alcohol groups to 1 acid group to 10 alcohol groups to 1 acid group. In other forms, the ratio of alcohol to acid groups in the esterification process may be from 9 to 1, or 7 to 1, or 5 to 1, or 3 to 1, or 2 to 1, or 1.5 to 1. Hence, in this advantageous form of the disclosed process, there is an excess of alcohol groups to acid groups. In the inventive process disclosed herein, the excess alcohol groups are separated in the fractionation step and recycled back to the esterification process.

The chemistry and a simplified process to produce triglycerides via the route described above is shown in equations (1)-(3), below. For simplicity, the branched hexene feed example is shown in eqn (1), but the feed can be linear or branched butene, pentenes, hexenes, heptenes, octenes or nonenes as the starting olefins. As discussed above, the resulting $C_4$, $C_5$, $C_6$, $C_7$, $C_8$, $C_9$, and $C_{10}$ acids may be used individually or together in mixtures to make mixed carbon number esters to be used as plasticizers as long as the sum of carbons for the triester groups ($R^1$, $R^2$, and $R^3$ plus three carbons for the three carbonyl groups and not including the three glycerol backbone carbons) for greater than or equal to 45 wt % of the plasticizer product is from 20 to 25. Correspondingly, the $C_4$-$C_{10}$ acids may be linear, branched, or a combination thereof. This mixing of carbon numbers and levels of branching may be manipulated to achieve the desired compatibility with PVC for the respective polyol used for the polar end of the plasticizer, and to meet other plasticizer performance properties.

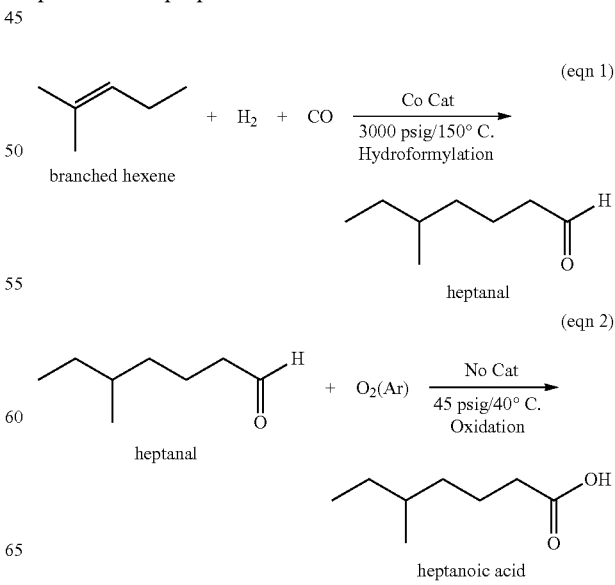

-continued

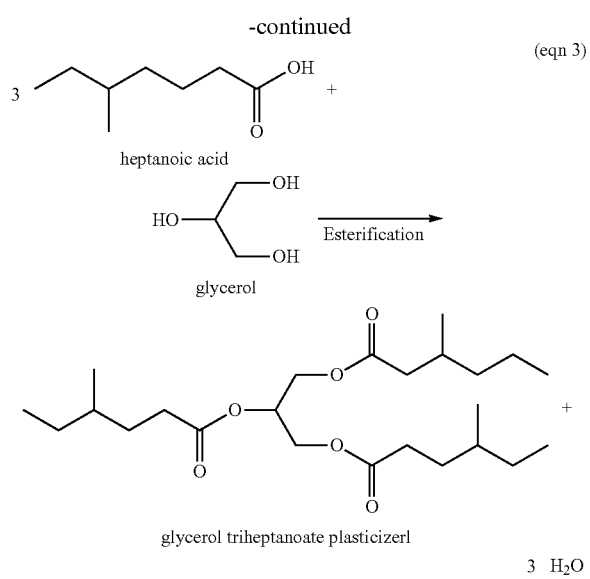

$$\text{(eqn 3)}$$

Equations 4-7 (designated 4-, 5-, 6- and 7-below) are as follows:

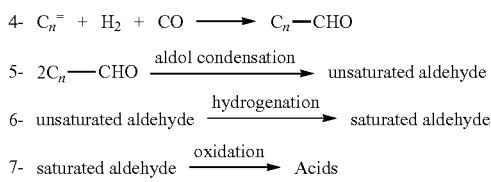

The applicability of the triglyceride structures as potential PVC plasticizers can be screened by estimating their relative solubility in PVC using Small's group contribution method to calculate solubility parameters for each structure (see The Technology of Plasticizers by J. Sears and J. Darbey, John Wiley & Sons, New York, 1982, pp 95-99, discussing using the Small formula to looking at plasticizer compatibility with PVC; this paper sites as a reference, the original work by Small: Small, P. A., "Some Factors Affecting the Solubility of Polymers", J. Appl. Chem, 3, pp 76-80 (1953); see also using Small's group contribution values from the Polymer Handbook, 3rd Ed., J. Brandrup & E. H. Immergut, Eds. John Wiley, New York, (1989)). These calculations are shown below in Table 1 for the C6 triglyceride (also referred to as 666 triglyceride):

TABLE 1

$C_6$ Triglyceride

|  | Solubility | Number | Solubility Contrib | MW | MW Contrib |
|---|---|---|---|---|---|
| $CH_3$ | 214 | 6 | 1284 | 15 | 90 |
| $—CH_2—$ | 133 | 8 | 1064 | 14 | 112 |
| $—CH=$ | 28 | 4 | 112 | 13 | 52 |
| COO esters | 310 | 3 | 930 | 44 | 132 |
|  |  |  | 3390 |  | 386 |

Solubility Parameter = 8.43
Delta to PVC = −1.23
Density = 0.96

However, the solubility parameter data alone does not predict both compatibility and volatility in PVC. The $C_6$ triglyceride (also referred to as 666 triglyceride) composition with a total carbon number of 18 (excluding the three glycerol backbone carbons) yields excessive volatility when used in PVC resins as a plasticizer, although compatibility is adequate.

Likewise, the solubility may also be calculated for the $C_7$ triglyceride (also referred to as 777 triglyceride), as shown in Table 2:

TABLE 2

$C_7$ Triglyceride

|  | Solubility | Number | Solubility Contrib | MW | MW Contrib |
|---|---|---|---|---|---|
| $CH_3$ | 214 | 6 | 1284 | 15 | 90 |
| $—CH_2—$ | 133 | 11 | 1463 | 14 | 154 |
| $—CH=$ | 28 | 4 | 112 | 13 | 52 |
| COO esters | 310 | 3 | 930 | 44 | 132 |
|  |  |  | 3789 |  | 428 |

Solubility Parameter = 8.50
Delta to PVC = −1.16
Density = 0.96

The $C_7$ triglyceride (also referred to as 777 triglyceride) composition with a total carbon number of 21 (excluding the three glycerol backbone carbons) yields adequate volatility and excellent compatibility when used in PVC resins as a plasticizer.

Table 3 shows the solubility values calculated by the same method for the $C_8$ triglyceride (also referred to as 888 triglyceride):

TABLE 3

$C_8$ Triglyceride

|  | Solubility | Number | Solubility Contrib | MW | MW Contrib |
|---|---|---|---|---|---|
| $CH_3$ | 214 | 6 | 1284 | 15 | 90 |
| $—CH_2—$ | 133 | 14 | 1862 | 14 | 196 |
| $—CH=$ | 28 | 4 | 112 | 13 | 52 |
| COO esters | 310 | 3 | 930 | 44 | 132 |
|  |  |  | 4188 |  | 470 |

Solubility Parameter = 8.55
Delta to PVC = −1.11
Density = 0.96

The $C_8$ triglyceride (also referred to as 888 triglyceride) composition with a total carbon number of 24 (excluding the three glycerol backbone carbons) yields adequate volatility and excellent compatibility when used in PVC resins as a plasticizer.

Table 4 shows the solubility values calculated by the same method for the $C_9$ triglyceride (also referred to as 999 triglyceride):

TABLE 4

$C_9$ Triglyceride

|  | Solubility | Number | Solubility Contrib | MW | MW Contrib |
|---|---|---|---|---|---|
| $CH_3$ | 214 | 6 | 1284 | 15 | 90 |
| $—CH_2—$ | 133 | 17 | 2261 | 14 | 238 |

TABLE 4-continued

C₉ Triglyceride

|  | Solubility | Number | Solubility Contrib | MW | MW Contrib |
|---|---|---|---|---|---|
| —CH═ | 28 | 4 | 112 | 13 | 52 |
| COO esters | 310 | 3 | 930 | 44 | 132 |
|  |  |  | 4587 |  | 512 |

Solubility Parameter = 8.6
Delta to PVC = −1.06
Density = 0.96

Again, however, the solubility parameter data alone does not predict both excellent compatibility and volatility in PVC. The $C_9$ triglyceride (also referred to as 999 triglyceride) composition with a total carbon number of 27 (excluding the three glycerol backbone carbons) yields adequate volatility, but inferior compatibility when used in PVC resins as a plasticizer.

The solubility parameter of PVC is calculated by the same Small's Group Contribution Method to be 9.66. The differences in solubility parameters between the triglyceride structures in FIG. 1 and PVC are shown in Tables 1-4. These differences from PVC range from 1.23 for the $C_6$ triglyceride (also referred to as 666 triglyceride) to 1.06 units for the $C_9$ triglyceride (also referred to as 999 triglyceride), which indicates reasonable expected solubility in PVC for these materials. As references, the solubility parameters for two well-known phthalate plasticizers, di-isononyl phthalate (DINP) and di-isodecyl phthalate (DIDP) are 8.88 (delta to PVC=0.78), and 8.56 (delta to PVC=1.10) respectively. The estimated solubility parameter for one non-phthalate plasticizer, di-isononyl cyclohexanoate, is 7.32 by Small's method. This is a difference of 2.34 solubility parameter units from PVC.

A non-limiting process embodiment is illustrated in FIG. 1. Propylene is used as feedstock to an oligomerization reaction. The reaction may be continuous, batch, or semibatch. Unreacted $C_3$ olefins are distilled off and optionally recycled. Trimers and tetramers may be recovered as bottoms product with the desired dimer hexene taken as a sidestream and send to the hydroformylation reaction. Carbon monoxide and hydrogen, conveniently supplied as Syngas, are also supplied to the reactor. The products are then separated by fractionation, with light olefins optionally recycled and the $C_7$ aldehydes and $C_7$ alcohols being separated. The amount of aldehyde and alcohols produced may be attenuated in the hydrofinishing section. In an embodiment, the $C_7$ aldehydes are then oxidized with the addition of air and/or oxygen, and unreacted aldehydes and heavies are separated out. The desired product $C_7$ acid is then esterified with polyol, in this embodiment glycerol and recovered as the triglyceride with a total carbon number (excluding the three glycerol backbone carbons) of the triester groups of 21.

In another form of the present disclosure, a composition comprising a blend of two or more different triglycerides may also provide outstanding plasticizer performance in range of polymer resins, including PVC. The blend of the two or more different triglycerides should include triglycerides according to the composition and process of making disclosed herein. That is, each triglyceride in the mixed triglyceride blend includes a linear or branched alkyl triglyceride; wherein the total carbon number of the triester groups ranges from 20 to 25. In one form, the mixed triglyceride includes a two component blend of 669/696 triglyceride and 699/969 triglyceride. In another form, the mixed triglyceride includes a two component blend of 5510/5105 triglyceride and 51010/10510 triglyceride. In yet another form, the mixed triglyceride includes a two component blend of 677/767 triglyceride and 777 triglyceride. Note however that these mixed triglyceride blends may include other proportions (defined herein as 55 wt % or less relative to the total) of triglycerides which do not have a total carbon number of the triester groups falling within the 20 to 25 range. If the total weight % of these non-inventive triglycerides is greater than 55 wt % in the mixed triglyceride blend, plasticizer properties (volatility, compatibility, low temperature performance, etc.) will begin to be negatively impacted. Hence, for the mixed triglycerides disclosed herein, linear or branched alkyl triglycerides with a total carbon number (excluding the three glycerol backbone carbons) of from 20 to 25 should comprise greater than or equal to 45 wt %, or greater than or equal to 60 wt %, or greater than or equal to 75 wt %, or greater than or equal to 90 wt %, or greater than or equal to 95 wt %, or greater than or equal to 97 wt %, or greater than or equal to 99 wt %, or greater than or equal to 99.5 wt %, or greater than or equal to 99.9 wt % of the mixed triglyceride blend. These mixed triglyceride blends may also be used as plasticizers and yield outstanding properties and performance with a variety of polymer resins.

The plasticizers according to the current disclosure may also be used with vinyl chloride-type resins, polyesters, polyurethanes, ethylene-vinyl acetate copolymer, rubbers, acrylics, polymer blends such as of polyvinyl chloride with an ethylene-vinyl acetate copolymer or polyvinyl chloride with a polyurethane or ethylene-type polymer. The plasticizers disclosed herein may be incorporated the aforementioned polymers by dryblending and then extrusion to form a resin composition. Other polymer additives chosen from stabilizers, fillers, pigments, biocides, carbon black, adhesion promoters, viscosity reducers, thixotropic agents, thickening agents, blowing agents, and mixtures thereof may also be added to the resin composition. In addition, the resin composition may further include additional plasticizers selected from phthalates, adipates, trimellitates, cyclohexanoates, benzoates, and combinations thereof.

EXAMPLES

General Procedure for Esterification

Into a four necked 1000 mL round bottom flask equipped with an air stirrer, nitrogen inductor, thermometer, Dean-Stark trap and chilled water cooled condenser were added 0.8 mole glycerol, 1.6 mole acid which has n carbons and 1.6 mole acid which has m carbons (n and m could be equal or the same and could be linear or branched). The Dean-Stark trap was filled with the lighter boiling acid to maintain the same molar ratio of acids in the reaction flask. The reaction mixture was heated to 220° C. with air stirring under a nitrogen sweep. The water collected in the Dean-Stark trap was drained frequently. The theoretical weight of water was obtained in about three hours at 220° C. indicating 96% conversion. The reaction mixture was heated an additional 10 hours for a total of 13 hours to achieve complete conversion to the triglycerides. The data are shown in the following figures. Composition for the triglyceride products is given in the following manner: a mixed triglyceride of acids with X and Y carbon numbers may theoretically contain products with three chains of length X (denoted XXX), three chains of length Y (denoted YYY), and products with mixed distributions (XXY, XYX, XYY, or YXY where the first and third character represent the terminal (primary) glyceride chains and the second character represents the internal (secondary) glyceride chain). The sum of the carbon numbers for the three chains (including the three carbonyl carbons and not including the three glycerol backbone carbons) ranges from 20 to 25 for the at least 45 wt % of the plasticizer product. Gas chromatography analysis on the products was conducted using a Hewlett-Packard 5890 GC equipped with a HP6890 autosampler, a HP flame-ionization detector, and a J&W Scientific DB-1 30 meter column (0.32 micrometer inner diameter, 1 micron film thickness, 100% dimethylpolysiloxane coating). The initial oven temperature was 60° C.; injector temperature 290° C.; detector temperature 300° C.; the temperature ramp rate from 60 to 300° C. was 10° C./minute with a hold at 300° C. for 14 minutes. The calculated %'s reported for products were obtained from peak area, with an FID detector uncorrected for response factors. Table 5 provides branching characteristics for the OXO acids used in the Examples.

TABLE 5

$^{13}$C NMR Branching Characteristics of Typical $C_7$-$C_{10}$ OXO Acids.

| OXO Acid | Average Carbon No. | Pendant Methyls[a] | Total Methyls[b] | Pendant Ethyls | % Carbonyls α to Branch |
|---|---|---|---|---|---|
| $C_7$ | 6.88-7.92 | 0.98-1.27 | 1.94-2.48 | 0.16-0.26 | 11.3-16.4 |
| $C_8$ | 8.1-8.3 | n/a | 2.7 | n/a | 12-15 |
| $C_9$ | 9.4 | n/a | n/a | n/a | 12 |
| $C_{10}$ | 10.2 | n/a | n/a | n/a | 12 |

[a]$C_1$ Branches.
[b]Includes methyls on all branch lengths and chain end methyls.

Illustrative Example 1

2.5 mole glycerol (Aldrich 99.5%) was esterified with 5.0 mole 2-methylvaleric acid (six carbons and branched) and 5.0 mole OXO $C_9$ acid (nine carbons, and linear, branched and mixtures thereof). After unreacted acid was distilled away, the mixture was extracted once with 10 wt % sodium carbonate solution at room temperature, then dried by stirring over 5 wt % magnesium sulfate for one hour. The mother solution was analyzed by GC. This solution was fractionated under vacuum.

Figure 2:
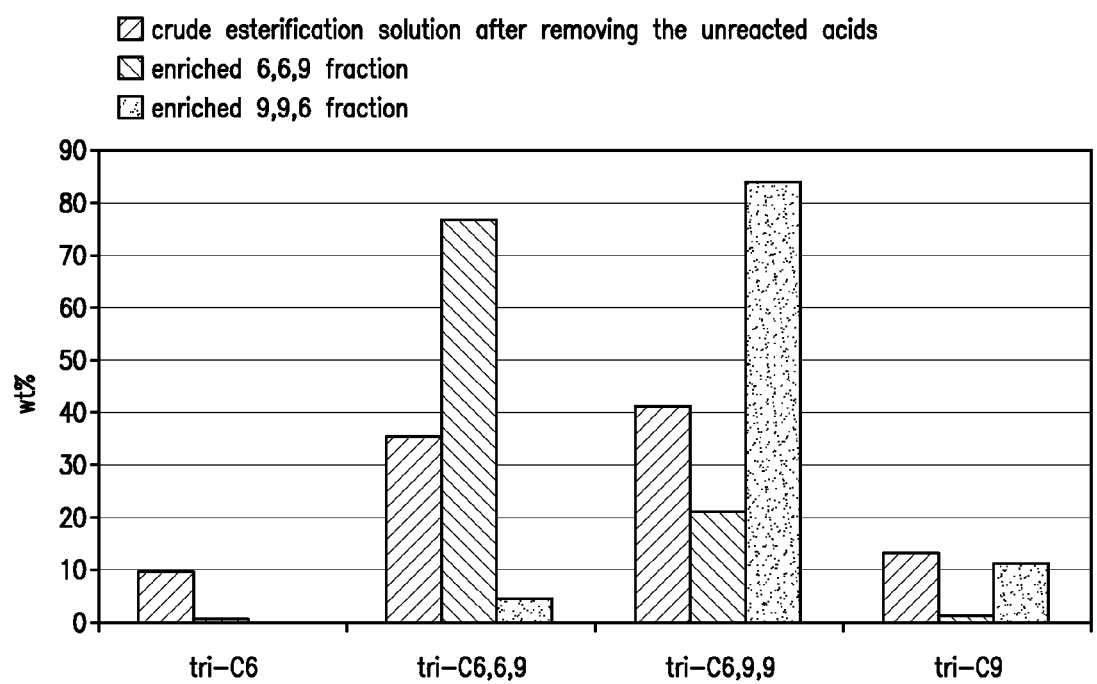
FIG. 2 is a graph of the composition of the combined fractions and the mother solution before distillation of Example 1.
Figure 3:
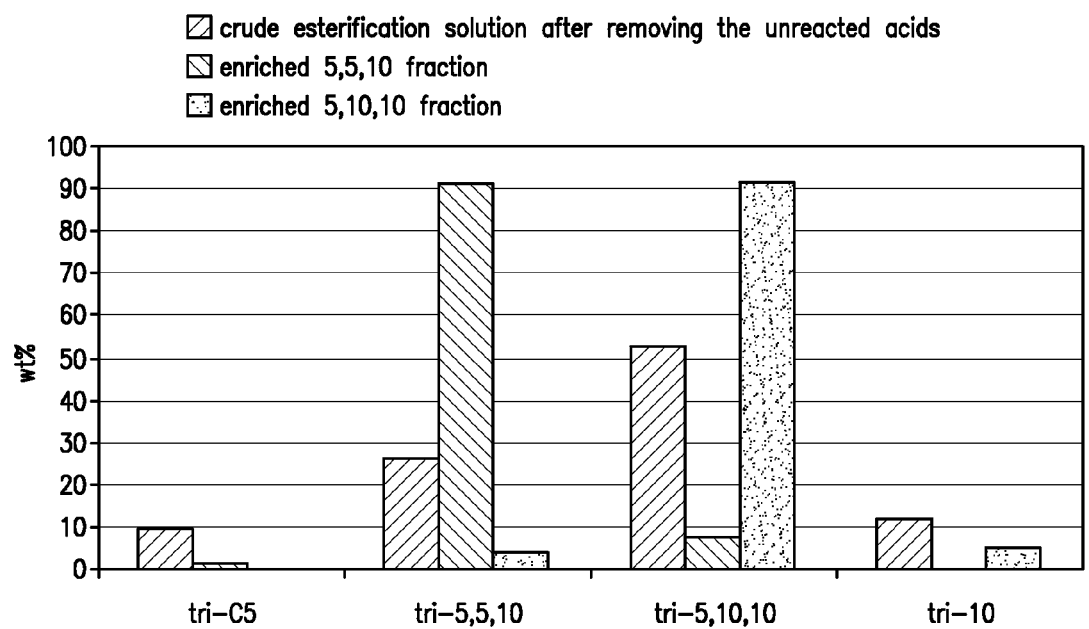
FIG. 3 is a graph of the composition of the combined fractions and the mother solution before distillation of Example 2.

Fractions which have similar composition were combined for plasticizing performance tests. The compositions of the combined fractions as determined by GC and the mother solution before distillation are shown in FIG. 2. The compositions of these triglyceride fractions are as follows:
Material 1-A: Unfractionated mother solution: 9.3% 666, 33.9% 669/696, 40.8% 699/969, 16.1% 999.
Material 1-B: 669/696-enriched product; 0.73% 666, 76.82% 669/696, 21.16% 699/969, 1.07% 999.
Material 1-C: 699/969-enriched product: 0.04% 666, 3.9% 669/696, 85.92% 699/969, 10.15% 999.

Illustrative Example 2

0.8 mole glycerol was esterified with 1.6 mole valeric acid (5 carbons and linear) and 1.6 mole OXO $C_{10}$ acid (10 carbons, and linear, branched and mixtures thereof). The unreacted acid was distilled. The mother solution was analyzed by GC. This solution was fractionated under vacuum.

Figure 4:
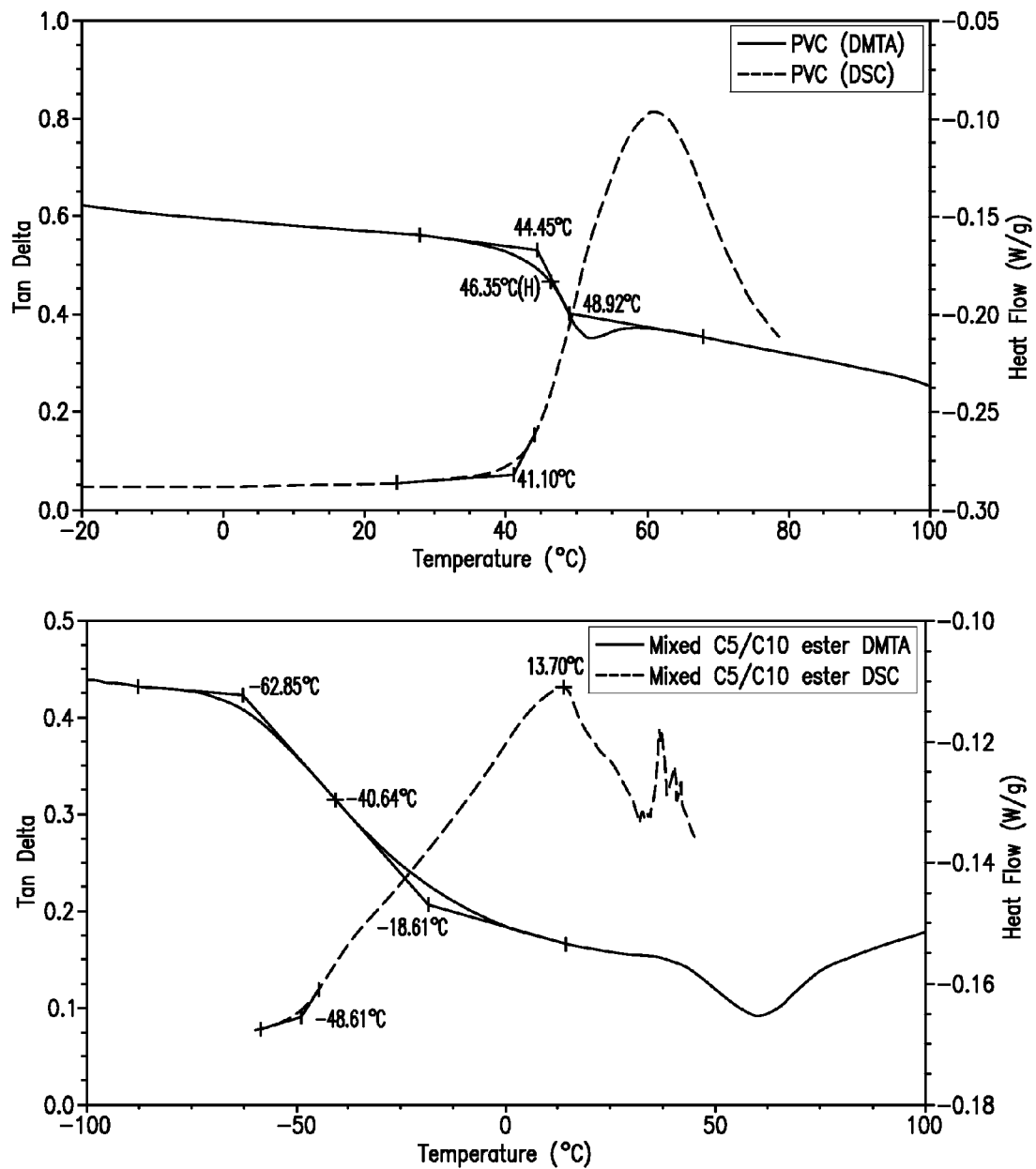
FIG. 4 shows Differential Scanning Calorimetry (DSC) curves (solid lines) for (top) neat PVC and (bottom) PVC plasticized with mixed triglyceride ester 2-B, overlaid with Dynamic Mechanical Thermal Analysis (DMTA) curves (dotted lines). Note: The tan delta onset value shown for the DMTA curve of neat PVC is a preliminary value; the actual value given in Table 9 is shown in FIG. 5.

Fractions which have similar composition where combined for plasticizing performance tests. The composition of the combined fractions and the mother solution before distillation are shown in FIG. 4. The compositions of these triglyceride fractions are as follows:
Material 2-A: Unfractionated mother solution; 8.4% 555, 33.3% 5510/5105, 40.9% 51010/10510, 17.0% 101010.
Material 2-B: 5510/5105-enriched product; 1.0% 555, 91.3% 5510/5105, 7.7% 51010/10510, 0% 101010.
Material 2-C: 51010/10510-enriched product; 0% 555, 3.8% 5510/5105, 91.5% 51010/10510, 4.7% 101010.

Illustrative Example 3

2.0 mole glycerol (Aldrich 99.5%) was esterified with 4.0 mole 2-methylvaleric acid (six carbons and branched) and 4.0 mole 3,5,5,-trimethylhexanoic acid (nine carbons and branched). The crude reaction mixture was fractionated by distillation. Aliquots of the distillate cuts were also recombined to provide a material with a composition representative of an unfractionated material, which was analyzed by GC (composition: 99.9% triglyceride and 0.1% diglyceride). The compositions of these triglyceride fractions and the representative recombined material are as follows:
Fraction 3-A: Recombined material representative of mother solution: 9.9% 666, 34.7% 669/969, 43.4% 699/969, 11.9% 999.
Fraction 3-B: 666 and 669/696-enriched product: 25.0% 666, 56.2% 669/696, 14.7% 669/969, 2.4% 999 and 0.1% C9 acid.
Fraction 3-C: 669/696-enriched product; 1.2% 666, 51.4% 669/696, 41.0% 669/969, 5.1% 999.
Fraction 3-D: 699/969-enriched product; 5.0% 669/696, 76.2% 699/969, 17.2% 999.
Fraction 3-E: 999-enriched product, 49.0% 699/969, 49.6% 999.

Illustrative Example 4

0.8 mole glycerol was esterified with 1.6 mole 2-methylvaleric acid (six carbons and branched) and 1.6 mole $C_7$ OXO acid (seven carbons, and linear, branched and mixtures thereof). The unreacted acid was distilled. The mother solution was analyzed by GC. The compositional data was as follows: 0.59% 666, 9.05% 667/676, 40.3% 677/767, 50.1% 777 (denoted as Fraction 4).

Comparative Example $C_1$

One mole glycerol was esterified with 3.3 mole 2-methylvaleric acid. The unreacted acid was distilled. The mother solution was analyzed by GC (99.8% 666 triglyceride). The plasticization of this material was not tested due to its unacceptable volatility.

Comparative Example $C_2$ 0.53 mole glycerol was esterified with 1.9 mole $C_9$ OXO acid. The unreacted acid was distilled. The mother solution was analyzed by GC (100% 999 triglyceride).

Comparative Example $C_3$ 1 mole glycerol was esterified with 3.3 mole 3,5,5-trimethylhexanoic acid. The unreacted acid was distilled. The mother solution was analyzed by GC (100% 999 triglyceride).

Comparative Example $C_4$ 1 mole glycerol was esterified with 3.3 mole $C_{10}$ OXO acid. The unreacted acid was distilled. The mother solution was analyzed by GC (99.86% 101010 triglyceride). The plasticization of this material was not tested due to the known poor compatibility of the 999 triglycerides.

Illustrative Example 5

One mole glycerol was esterified with a blend of 0.67 mole valeric acid (n-pentanoic acid), 0.67 mole 2-methylvaleric acid, 0.67 mole $C_7$ OXO acid, 0.67 mole $C_8$ OXO acid, 0.67 mole $C_9$ OXO acid, and 0.67 mole $C_{10}$ OXO acid. The unreacted acid was distilled. The mother solution was analyzed by GC (100% triglycerides) and contained the possible mixed triglyceride isomers of the various sidechains. Quantification of the isomer distribution was not possible; however, a similar triglyceride material prepared with linear $C_5$-$C_{10}$ acids had 67.74 wt % $C_{20}$-$C_{25}$ triglycerides by GC; it is assumed the content of this product is similar.

Illustrative Example 6

General Procedure for the Use of Mixed Triglyceride Esters to Plasticize Poly(Vinyl Chloride)

A 4.5 g portion of the ester sample was weighed into an Erlenmeyer flask which had previously been rinsed with uninhibited tetrahydrofuran (THF) to remove dust. A 0.63 g portion of a 70:30 by weight solid mixture of powdered Drapex® 6.8 (Crompton Corp.) and Mark® 4716 (Chemtura USA Corp.) stabilizers was added along with a stirbar. The solids were dissolved in 90 mL uninhibited THF. Oxy Vinyls® 240F PVC (9.0 g) was added in powdered form and the contents of the flask were stirred overnight at room temperature until dissolution of the PVC was complete (a PVC solution for preparation of an unplasticized comparative sample was prepared using an identical amount of stabilizer, 100 mL solvent, and 13.5 g PVC). The clear solution was poured evenly into a flat aluminum paint can lid (previously rinsed with inhibitor-free THF to remove dust) of dimensions 7.5" diameter and 0.5" depth. The lid was placed into an oven at 60° C. for two hours with a moderate nitrogen purge. The pan was removed from the oven and allowed to cool for a ~5 min period. The resultant clear film was carefully peeled off of the aluminum, flipped over, and placed back evenly into the pan. The pan was then placed in a vacuum oven at 70° C. overnight to remove residual THF. The dry, flexible, almost colorless film was carefully peeled away and exhibited no oiliness or inhomogeneity, except where noted in the Tables. The film was cut into small pieces to be used for preparation of test bars by compression molding (size of pieces was similar to the hole dimensions of the mold plate). The film pieces were stacked into the holes of a multi-hole steel mold plate, pre-heated to 170° C., having hole dimensions 20 mm×12.8 mm×1.8 mm (ASTM D1693-95 dimensions). The mold plate was pressed in a PHI company QL-433-6-M2 model hydraulic press equipped with separate heating and cooling platforms. The upper and lower press plates were covered in Teflon™-coated aluminum foil and the following multistage press procedure was used at 170° C. with no release between stages: (1) three minutes with 1-2 ton overpressure; (2) one minute at 10 tons; (3) one minute at 15 tons; (4) three minutes at 30 tons; (5) release and three minutes in the cooling stage of the press (7° C.) at 30 tons. A knockout tool was then used to remove the sample bars with minimal flexion. Near-colorless, flexible bars were obtained which, when stored at room temperature, showed no oiliness or exudation several weeks after pressing, except where noted in the Tables. The bars were allowed to age at room temperature for at least one week prior to evaluation of phase behavior with Differential Scanning Calorimetry (DSC) and thermo-physical properties with Dynamic Mechanical Thermal Analysis (DMTA).

Illustrative Example 7

Differential Scanning Calorimetry (DSC) and Thermogravimetric Analysis (TGA) Property Study of Mixed Triglyceride Esters Thermogravimetric Analysis (TGA) was conducted on the neat esters prepared in Examples 1-4 and small portions of the neat and plasticized PVC bars prepared in Example 6, using a TA Instruments AutoTGA 2950HR instrument (25-600° C., 10° C./min, under 60 cc $N_2$/min flow through furnace and 40 cc $N_2$/min flow through balance; sample size 10-20 mg). Table 6 provides a volatility comparison of the different ester fractions. Table 7 provides a volatility comparison of the neat and plasticized PVC bars prepared in Example 6. Differential Scanning Calorimetry (DSC) was also performed on the neat plasticizers, using a TA Instruments 2920 calorimeter fitted with a liquid $N_2$ cooling accessory. Samples were loaded at room temperature and cooled to about –130° C. at 10° C./min and analyzed on heating to 75° C. at a rate of 10° C./min. Table 6 provides a glass transition ($T_g$) comparison of the different ester fractions. $T_g$s given in Table 6 are midpoints of the second heats (unless only one heat cycle was performed, in which case the first heat $T_g$, which is typically in very close agreement, is given).

TABLE 6

Volatility and Glass Transition Properties of Mixed Triglyceride Esters.

| Sample | TGA 1% Wt Loss (° C.) | TGA 5% Wt Loss (° C.) | TGA 10% Wt Loss (° C.) | TGA Wt Loss at 220° C. (%) | DSC $T_g$ (° C.) |
|---|---|---|---|---|---|
| 1-A | 167.4 | 200.7 | 216.7 | 11.5 | −89.9 |
| 1-B | 165.5 | 198.9 | 213.2 | 13.7 | −91.1 |
| 1-C | 182.0 | 212.4 | 227.1 | 7.2 | −87.0 |
| 2-A | 171.7 | 203.7 | 219.3 | 10.3 | −89.6 |
| 2-B | 159.4 | 191.8 | 205.9 | 19.1 | −91.6 |
| 2-C | 175.7 | 212.7 | 227.9 | 7.0 | −85.4 |
| 3-A | 150.0 | 184.6 | 199.7 | 23.8 | −82.7 |
| 3-B | — | — | — | — | — |
| 3-C | — | — | — | — | — |
| 3-D | — | — | — | — | — |
| 3-E | — | — | — | — | — |
| 4 | 162.3 | 191.3 | 205.5 | 19.0 | −93.1 |
| 5 | 172.8 | 204.0 | 218.9 | 10.5 | −88.9 |
| $C_1$ | — | — | — | 47.4 | −97.1 |
| $C_2$ | 172.4 | 220.8 | 236.4 | 4.8 | −82.1 |
| $C_3$ | — | 212.7 | 228.7 | 6.8 | −68.1 |
| $C_4$ | — | — | — | 2.2 | −79.6 |

— Data not obtained.

TABLE 7

Volatility Properties of Neat PVC and PVC Sample Bars Plasticized With Mixed Triglyceride Esters.

| Plasticizer Used in Bar | TGA 1% Wt Loss (° C.) | TGA 5% Wt Loss (° C.) | TGA 10% Wt Loss (° C.) | TGA % Wt Loss at 220° C. |
|---|---|---|---|---|
| None (Neat PVC) | 129.9 | 192.3 | 255.4 | 6.3 |

TABLE 7-continued

Volatility Properties of Neat PVC and PVC
Sample Bars Plasticized With Mixed Triglyceride Esters.

| Plasticizer Used in Bar | TGA 1% Wt Loss (° C.) | TGA 5% Wt Loss (° C.) | TGA 10% Wt Loss (° C.) | TGA % Wt Loss at 220° C. |
|---|---|---|---|---|
| 1-A | 193.1 | 236.0 | 256.4 | 2.9 |
| 1-B | 185.2 | 225.1 | 252.3 | 4.2 |
| 1-C | 199.9 | 244.4 | 256.8 | 2.1 |
| 2-A | 185.9 | 233.0 | 246.5 | 3.5 |
| 2-B | 185.5 | 226.0 | 244.1 | 4.2 |
| 2-C | 204.3 | 242.0 | 251.1 | 1.9 |
| 3-A* | 188.5 | 233.3 | 251.8 | 3.4 |
| 3-B* | 173.6 | 213.5 | 245.0 | 5.8 |
| 3-C* | 180.8 | 218.1 | 251.0 | 5.3 |
| 3-D* | 196.9 | 239.9 | 260.8 | 2.7 |
| 3-E* | 196.7 | 242.6 | 261.0 | 2.6 |
| 4 | 180.5 | 218.8 | 241.2 | 5.2 |
| 5 | 190.2 | 229.9 | 250.6 | 2.0 |
| $C_1$ | Not made | Not made | Not made | Not made |
| $C_2$* | — | — | — | — |
| $C_3$** | Not made | Not made | Not made | Not made |
| $C_4$ | Not made | Not made | Not made | Not made |

— Data not obtained.
*Sample bars of $C_2$, 3-A, 3-D, and 3-E were oily; sample bars of fractions 3-B and 3-C were also noted to be slightly oily or oily after long storage periods and/or DMTA analysis.
**The cast film of PVC/$C_3$ was oily/hazy; no sample bar was prepared.

Illustrative Example 8

Demonstration of Plasticization of PVC with Triglyceride Esters Via Differential Scanning Calorimetry (DSC)

Differential Scanning Calorimetry (DSC) was performed on the compression-molded sample bars prepared in Example 6 (PVC:plasticizer ratio 2:1) using a TA Instruments 2920 calorimeter fitted with a liquid $N_2$ cooling accessory. Samples were loaded at room temperature and cooled to −90° C. at 10° C./min, and then analyzed on heating at a rate of 10° C./min to 150-170° C. for plasticized PVC bars, and to 100° C. for the comparative neat PVC bar. Small portions of the sample bars (typical sample mass 5-7 mg) were cut for analysis, making only vertical cuts perpendicular to the largest surface of the bar to preserve the upper and lower compression molding "skins"; the pieces were then placed in the DSC pans so that the upper and lower "skin" surfaces contacted the bottom and top of the pan. Table 8 provides the first heat $T_g$ onset, midpoint, and end for neat PVC and the plasticized bars. A lowering and broadening of the glass transition for neat PVC is observed upon addition of the esters, indicating plasticization and extension of the flexible temperature range of use for neat PVC (for aid in calculating the numerical values of these broad transitions, the DSC curve for each plasticized bar was overlaid with the analogous Dynamic Mechanical Thermal Analysis (DMTA) curve, taken and analyzed as described in Example 9, since the DMTA curve provides additional guidance about the proper temperature regions for the onset, midpoint, and end of $T_g$). FIG. 4 shows DSC curves for neat PVC and a typical curve for a plasticized bar (containing material 2-B), overlaid with representative analogous DMTA curves.

TABLE 8

Glass Transition Onset, Midpoint, and End
for Plasticized PVC Bars

| Plasticizer Used in Bar | $T_g$ Onset (° C.) | $T_g$ Midpt (° C.) | $T_g$ End (° C.) | $T_m$ Max (° C.) and $\Delta H_f$ (J/g)$^a$ |
|---|---|---|---|---|
| None (Neat PVC) | 44.5 | 46.4 | 48.9 | not calc. |
| 1-A | −10.5 | −6.3 | −5.9 | not calc. |
| 1-B | −52.2 | −29.6 | −12.7 | 56.7 (1.00) |
| 1-C | −49.9 | −27.9 | −10.1 | 53.9 (0.85) |
| 2-A | −63.9 | −40.1 | −16.3 | not calc. |
| 2-B | −62.9 | −40.6 | −18.6 | not calc. |
| 2-C | −61.5 | −41.3 | −21.8 | 61.6 (0.99) |
| 3-A* | — | — | — | — |
| 3-B* | −28.2 | −17.3 | −6.3 | not calc. |
| 3-B* | −27.7 | −15.4 | −3.3 | 55.6 (0.77) |
| 3-D* | −28.6 | −14.8 | −0.9 | 52.3 (0.77) |
| 3-E* | −27.0 | −14.5 | −2.0 | not calc. |
| 4 | −60.7 | −42 | −23.4 | not calc. |
| $C_1$ | Not made | Not made | Not made | Not made |
| $C_2$* | — | — | — | — |
| $C_3$** | Not made | Not made | Not made | Not made |
| $C_4$ | Not made | Not made | Not made | Not made |

— Data not obtained.
*Sample bars of $C_2$, 3-A, 3-D, and 3-E were oily; sample bars of fractions 3-B and 3-C were also noted to be slightly oily or oily after long storage periods and/or DMTA analysis.
**The cast film of PVC/$C_3$ was oily/hazy; no sample bar was prepared.
$^a$Most sample bars showed a weak melting point ($T_m$) from the crystalline portion of PVC. Often this weak transition was not specifically analyzed; but data is given here in instances where it was recorded.

Illustrative Example 9

Demonstration of Plasticization of PVC with Mixed Triglyceride Esters Via Dynamic Mechanical Thermal Analysis (DMTA)

Three-point bend Dynamic Mechanical Thermal Analysis (DMTA) with a TA Instruments DMA Q980 fitted with a liquid $N_2$ cooling accessory and a three-point bend clamp assembly was used to measure the thermo-mechanical performance of neat PVC and the PVC/plasticizer blend sample bars prepared in Example 6. Samples were loaded at room temperature and cooled to −60° C. at a cooling rate of 3° C./min. After equilibration, a dynamic experiment was performed at one frequency using the following conditions: 3° C./min heating rate, 1 Hz frequency, 20 micrometer amplitude, 0.01 pre-load force, force track 120%. Two or three bars of each sample were typically analyzed; numerical data was taken from the bar typically exhibiting the highest room temperature storage modulus (the bar assumed to have the fewest defects). Glass transition onset values were obtained by extrapolation of the tan delta curve from the first deviation from linearity. The DMTA measurement gives storage modulus (elastic response modulus) and loss modulus (viscous response modulus); the ratio of loss to storage moduli at a given temperature is tan delta. The beginning (onset) of the $T_g$ (temperature of brittle-ductile transition) was obtained for each sample by extrapolating a tangent from the steep inflection of the tan delta curve and the first deviation of linearity from the baseline prior to the beginning of the peak. Table 9 provides a number of DMTA parameters for neat PVC and PVC bars plasticized with triglyceride esters: $T_g$ onset (taken from tan delta); peak of the tan delta curve; storage modulus at 25° C.; and the temperature at which the storage modulus equals 100 MPa (this temperature was chosen to provide an arbitrary measure of the temperature at which the PVC loses a set amount of rigidity; too much loss of rigidity may lead to processing complications for the PVC material). The flexible use temperature range of the plasticized PVC samples is evaluated as the range between the $T_g$ onset and the temperature at which the storage modulus was 100 MPa. A lowering and broadening of the glass transition for neat PVC is observed upon addition of the esters, indicating plasticization and extension of the flexible temperature range of use for neat PVC. Plasticization (enhanced flexibility) is also demonstrated by lowering of the PVC room temperature storage modulus upon addition of the esters.

Figure 5:
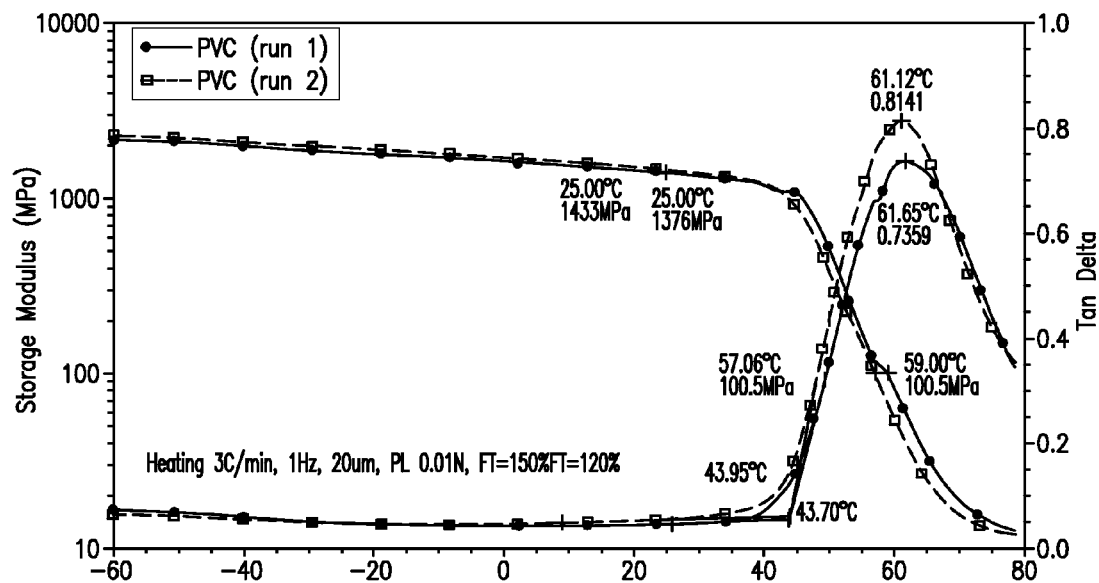
FIG. 5 shows Dynamic Mechanical Thermal Analysis curves for (top) neat PVC and (bottom) PVC plasticized with mixed triglyceride ester 2-B. For each material, two repeat runs are shown.
Figure 5:
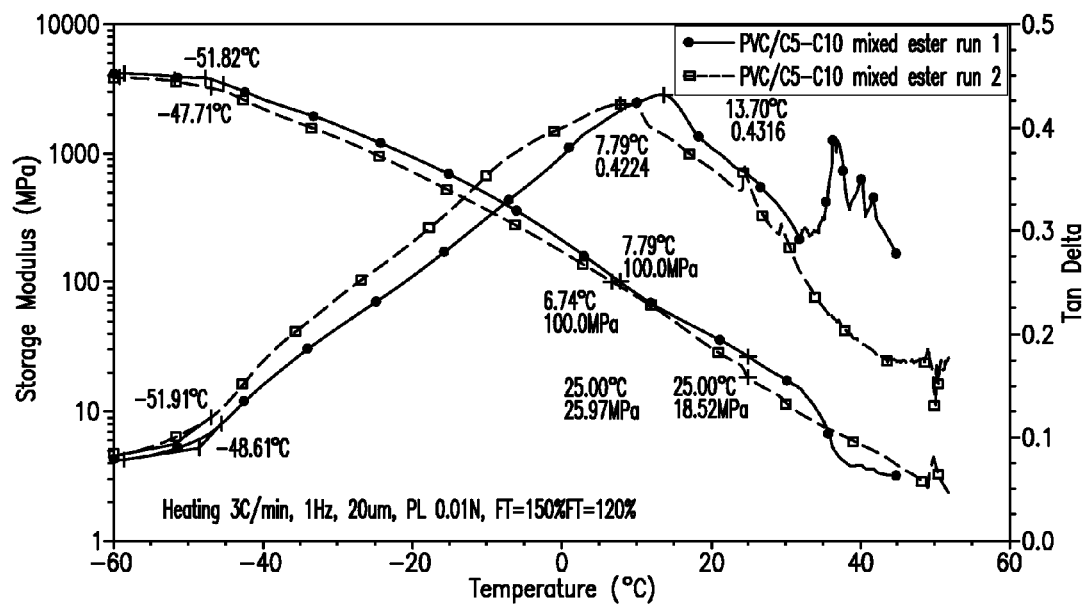

FIG. 5 shows DMTA tan delta and storage modulus curves versus temperature for neat PVC and PVC plasticized with a typical mixed triglyceride (material 2-B). Differences in blend performance (shape of the tan delta and storage modulus versus temperature curves) in the temperature range between −40 and −20° C. are likely to be optimizable by adjusting the ratio of PVC to ester in the blend.

TABLE 9

Various DMTA Thermal Parameters for PVC Bars Plasticizer with Mixed Triglyceride Esters

| Plasticizer Used in Bar | Tan Δ $T_g$ Onset (° C.) | Tan Δ Peak (° C.) | 25° C. Storage Mod. (MPa) | Temp. of 100 MPa Storage Mod. (° C.) | Flexible Use Range (° C.)$^a$ |
|---|---|---|---|---|---|
| None (Neat PVC) | 44.0 | 61.1 | 1433 | 57.1 | 13.1 |
| 1-A | −41.0 | 23.5 | 56.2 | 16.6 | 57.6 |
| 1-B | −41.8 | 18.0 | 56.2 | 19.8 | 61.6 |
| 1-C | −42.1 | 39.2 | 64.9 | 19.7 | 61.8 |
| 2-A | −49.3 | 21.4 | 50.2 | 15.4 | 64.7 |
| 2-B | −48.6 | 13.7 | 26.0 | 7.8 | 56.4 |
| 2-C | −45.9 | 30.5 | 81.1 | 22.3 | 68.2 |
| 3-A* | −46.8 | 42.7 | 153.1 | 30.3 | 77.1 |
| 3-B* | −42.8 | 29.4 | 70.3 | 21.5 | 64.3 |
| 3-C* | −41.5 | 31.8 | 104.7 | 25.5 | 67.0 |
| 3-D* | −35.5 | 54.6 | 383.7 | 41.8 | 77.3 |
| 3-E* | −18.3 | 56.2 | 376.8 | 43.8 | 62.1 |
| 4 | −48.3 | 15.2 | 37.9 | 12.9 | 61.2 |
| 5 | −49.1 | 29.4 | 69.5 | 19.8 | 68.9 |

— Data not obtained.
*Sample bars of fractions 3-A, 3-D, and 3-E were oily; sample bars of fractions 3-B and 3-C were also noted to be slightly oily or oily after long storage periods and/or DMTA analysis.
$^a$Difference between temperature of 100 MPa storage modulus and onset of $T_g$.

Illustrative Example 10

Procedure for the Recycled Acid, Mono- and Di-Glycerides

The general procedure was applied using neoheptanoic acid plus glycerol at 197-210° C. to synthesize triglyceride. After 5 hours runtime approx. 89% conversion was achieved. The reaction mixture was then transferred to a distillation flask and distilled under vacuum to 0.10 mm with the aid of an 18 inch Vigreaux column. The distillates contained neoheptanoic acid, mono-, di- and triglycerides and were combined. The composition by gc analysis was as follow: Neoheptanoic acid (675.7 grams, 5.2 mole), Mono-$C_7$ glyceride (11.03 grams, 0.054 mole), Di-$C_7$ glyceride (79.71 grams, 0.252 mole), Tri-$C_7$ glyceride (61.13 g, 0.143 mole).

The residue after distillation contained approx. 344 grams of triglycerides with a purity of 99.9%.

Into a four necked 1000 ml round bottom flask equipped with an air stirrer, nitrogen inductor, thermometer, Dean-Stark trap and chilled water cooled condenser were added the above mixture of recovered neoheptanoic acid, mono-, di- and triglycerides plus fresh glycerol (74.1 grams, 0.81 mole). The reaction was conducted in the same manner as the general procedure for esterification. After 5 hours runtime approx. 90.7% conversion was achieved.

The composition of the reaction mixture after 5 hour heating is indicated in Table 10 below:

TABLE 10

Composition of reaction mixture

| | 1st Run, fresh reactants | 2nd Run, recycled reactants + glycerol |
|---|---|---|
| monoglycerides | 1.9% | 1.1% |
| diglycerides | 18% | 15% |
| triglycerides | 80% | 84% |

After only one recycle the steady state has not been established. FIG. 7 indicates the rates of esterification based on the water removed from the Dean-Stark trap.

PCT and EP Claims:

1. A process for producing a plasticizer comprising: (i) recovering at least one linear $C_4$ to $C_{10}$ aldehyde, one branched $C_4$ to $C_{10}$ aldehyde, or a combination thereof from a hydroformylation product; (ii) oxidizing the linear, branched or combination thereof $C_4$ to $C_{10}$ aldehyde to form a linear, branched or combination thereof $C_4$ to $C_{10}$ acid; (iii) esterifying the linear, branched or combination thereof $C_4$ to $C_{10}$ acid with a polyol to yield a linear alkyl triglyceride, a branched alkyl triglyceride, or a combination thereof, and reaction byproducts; (iv) purifying the linear, branched or combination thereof alkyl triglyceride to form a plasticizer stream, a reaction byproduct stream, and an unreacted input stream, wherein the total carbon number of the triester groups ranges from 20 to 25 for greater than or equal to 45 wt % of the plasticizer; and (v) recycling from the purifying step back to the esterifying step the unreacted input stream and the reaction byproduct stream.

2. The process of clause 1, wherein the ratio of alcohol groups from the polyol to acid groups from the $C_4$ to $C_{10}$ acid in the esterifying step ranges from 1 to 1.1 to 1 to 10 to provide an excess of acid groups to alcohol groups.

3. The process of clauses 2 or 3, wherein the unreacted input stream includes unreacted $C_4$ to $C_{10}$ acid.

4. The process of clauses 2 or 3, wherein the reaction byproduct stream includes alkyl triglyceride with a total carbon number of the triester groups less than 20, and triglyceride with a total carbon number of the triester groups greater than 25.

5. The process of clause 2, 3, or 4, wherein the reaction rate of the esterifying step is substantially similar to the reaction rate without the recycle of the unreacted $C_4$ to $C_{10}$ acid.

6. The process of clause 1, wherein the ratio of alcohol groups from the polyol to acid groups from the $C_4$ to $C_{10}$ acid in the esterifying step ranges from 1 to 1 to 10 to 1.

7. The process of clause 6, wherein the unreacted input stream includes unreacted polyol.

8. The process of clauses 6 or 7, wherein the reaction byproduct stream includes monoglyceride, diglyceride, alkyl triglyceride with a total carbon number of the triester groups less than 20, and triglyceride with a total carbon number of the triester groups greater than 25.

9. The process of clause 8, wherein the reaction byproduct stream of the esterifying step also includes olefins, aldehydes, ketones, ethers and combinations thereof.

10. A process for producing a plasticizer comprising: (i) recovering an aldehyde/alcohol mixture including at least one linear $C_4$ to $C_{10}$ aldehyde, one branched $C_4$ to $C_{10}$ aldehyde, or a combination thereof and at least one linear $C_4$ to $C_{10}$ alcohol, one branched $C_4$ to $C_{10}$ alcohol, or a combination thereof from a hydroformylation process; (ii) oxidizing the aldehyde/alcohol mixture to form a linear, branched or combination thereof $C_4$ to $C_{10}$ acid; (iii) esterifying the linear, branched or combination thereof $C_4$ to $C_{10}$ acid with a polyol to yield a linear alkyl triglyceride, a branched alkyl triglyceride, or a combination thereof, and reaction byproducts; (iv) purifying the linear, branched or combination thereof alkyl triglyceride to form a plasticizer stream, a reaction byproduct stream and an unreacted input stream, wherein the total carbon number of the triester groups ranges from 20 to 25 for greater than or equal to 45 wt % of the plasticizer; and (v) recycling from the purifying step back to the esterifying step the unreacted input stream and the reaction byproduct stream.

11. The process of clause 10, wherein the ratio of alcohol groups from the polyol to acid groups from the $C_4$ to $C_{10}$ acid in the esterifying step ranges from 1 to 1.1 to 1 to 10 to provide an excess of acid groups to alcohol groups.

12. The process of clause 10 or 11, wherein the unreacted input stream includes unreacted $C_4$ to $C_{10}$ acid.

13. The process of clauses 11 or 12, wherein the reaction byproduct stream includes alkyl triglyceride with a total carbon number of the triester groups less than 20, and triglyceride with a total carbon number of the triester groups greater than 25.

14. The process of clause 11, 12 or 13, wherein the reaction rate of the esterifying step is substantially similar to the reaction rate without the recycle of the unreacted $C_4$ to $C_{10}$ acid.

15. The process of clause 10, wherein the ratio of alcohol groups from the polyol to acid groups from the $C_4$ to $C_{10}$ acid in the esterifying step ranges from 1 to 1 to 10 to 1.

16. The process of clause 15, wherein the unreacted input stream includes unreacted polyol.

17. The process of clauses 15 or 16, wherein the reaction byproduct stream includes monoglyceride, diglyceride, alkyl triglyceride with a total carbon number of the triester groups less than 20, and triglyceride with a total carbon number of the triester groups greater than 25.

18. The process of clauses 15, 16 or 17, wherein the reaction byproduct stream of the esterifying step also includes olefins, aldehydes, ketones, ethers and combinations thereof.

19. A process for producing a plasticizer comprising: (i) recovering at least one linear $C_4$ to $C_{10}$ aldehyde, one branched $C_4$ to $C_{10}$ aldehyde, or a combination thereof from a hydroformylation product; (ii) oxidizing the linear, branched or combination thereof $C_4$ to $C_{10}$ aldehyde to form a linear, branched or combination thereof $C_4$ to $C_{10}$ acid; (iii) esterifying the linear, branched or combination thereof $C_4$ to $C_{10}$ acid with a polyol to yield a linear alkyl triglyceride, a branched alkyl triglyceride, or a combination thereof, and monoglyceride, and diglyceride; (iv) purifying the linear, branched or combination thereof alkyl triglyceride to form a plasticizer, wherein the total carbon number of the triester groups ranges from 20 to 25 for greater than or equal to 45 wt % of the plasticizer; and (v) recycling from the purifying step back to the esterifying step unreacted $C_4$ to $C_{10}$ acid, unreacted polyol, monoglyceride, diglyceride, alkyl triglyceride with a total carbon number of the triester groups less than 20, and triglyceride with a total carbon number of the triester groups greater than 25.

All patents and patent applications, test procedures (such as ASTM methods, UL methods, and the like), and other documents cited herein are fully incorporated by reference to the extent such disclosure is not inconsistent with this invention and for all jurisdictions in which such incorporation is permitted.

When numerical lower limits and numerical upper limits are listed herein, ranges from any lower limit to any upper limit are contemplated. While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

The invention has been described above with reference to numerous embodiments and specific examples. Many variations will suggest themselves to those skilled in this art in light of the above detailed description. All such obvious variations are within the full intended scope of the appended claims.

What is claimed is:

1. A process for producing a plasticizer comprising:
   (i) recovering at least one linear $C_4$ to $C_{10}$ aldehyde, one branched $C_4$ to $C_{10}$ aldehyde, or a combination thereof from a hydroformylation product;
   (ii) oxidizing the linear, branched or combination thereof $C_4$ to $C_{10}$ aldehyde to form a linear, branched or combination thereof $C_4$ to $C_{10}$ acid;
   (iii) esterifying the linear, branched or combination thereof $C_4$ to $C_{10}$ acid with a polyol to yield a linear alkyl triglyceride, a branched alkyl triglyceride, or a combination thereof, and reaction byproducts;
   (iv) purifying the linear, branched or combination thereof alkyl triglyceride to form a plasticizer stream, a reaction byproduct stream, and an unreacted input stream, wherein the total carbon number of the alkyl triester groups ranges from 20 to 25 for greater than or equal to 45 wt % of the plasticizer; and
   (v) recycling from the purifying step back to the esterifying step the unreacted input stream and the reaction byproduct stream.

2. The process of claim 1, wherein the at least one branched $C_4$ to $C_{10}$ aldehyde is characterized by a branching of from about 0.8 to about 3.0 branches per molecule.

3. The process of claim 1, wherein the oxidizing step is with oxygen and/or air.

4. The process of claim 1, further including recovering at least one linear $C_4$ to $C_{10}$ alcohol, one branched $C_4$ to $C_{10}$ alcohol, or a combination thereof from the hydroformylation product, oxidizing the linear, branched or combination thereof $C_4$ to $C_{10}$ alcohol to form a linear, branched or combination thereof $C_4$ to $C_{10}$ acid; and feeding the linear, branched or combination thereof $C_4$ to $C_{10}$ acid to step (iii) of claim 1.

5. The process of claim 1, wherein the hydroformylation product includes a mixture of at least one linear $C_4$ to $C_{10}$ aldehyde, one branched $C_4$ to $C_{10}$ aldehyde, or a combination thereof and at least one at least one linear $C_4$ to $C_{10}$ alcohol, one branched $C_4$ to $C_{10}$ alcohol, or a combination thereof.

6. The process of claim 1, further including purifying the linear, branched or combination thereof $C_4$ to $C_{10}$ acid of step (ii) from the unreacted branched or combination thereof $C_4$ to $C_{10}$ aldehyde via distillation before the esterifying step (iii).

7. The process of claim 1, wherein the polyol is selected from glycerol, ethylene glycol, and propylene glycol, and mixtures thereof.

8. The process of claim 7, wherein the polyol comprises glycerol.

9. The process of claim 1, further comprising providing a feed for the hydroformylation process from dimerization of a feedstock.

10. The process of claim 9, wherein the feedstock comprises an olefin selected from propylene, butenes, pentenes and mixtures thereof.

11. The process of claim 9, wherein the hydroformylation reaction is catalyzed by a metal selected from Groups 8-10 according to the new notation for the Periodic Table as set forth in Chemical Engineering News, 63(5), 27 (1985).

12. The process of claim 11, wherein the hydroformylation reaction is catalyzed by a metal selected from Rh, Co, and mixtures thereof.

13. The process of claim 12, wherein the hydroformylation reaction is catalyzed by a metal selected from Rh, Co, and mixtures thereof including an organic ligand.

14. The process of claim 1, wherein the total carbon number of the triester groups ranges from 20 to 25 for greater than or equal to 75 wt % of the plasticizer.

15. The process of claim 14, wherein the total carbon number of the triester groups ranges from 20 to 25 for greater than or equal to 95 wt % of the plasticizer.

16. The process of claim 1, wherein the oxidizing step is catalyzed.

17. The process of claim 1, wherein the oxidizing step is not catalyzed.

18. The process of claim 1, wherein the esterifying step is catalyzed by at least one metal selected from Ti, Zr or Sn, or a mixture thereof, or catalyzed by an organic acid.

19. The process of claim 1, further comprising dimerizing a feedstock selected from propylene, butenes, pentenes and mixtures thereof by solid phosphoric acid or a zeolite dimerization to provide a feed for the hydroformylation process.

20. A plasticizer made by the process of claim 1, wherein the average branching of the alkyl triester groups ranges from about 1.2 to about 3.0 and with the proviso that the plasticizer is substantially free of aryl triglyceride.

21. The plasticizer of claim 20 characterized as being phthalate-free.

22. A resin composition comprising the plasticizer of claim 20 and a resin.

23. The resin composition of claim 22, wherein the resin is selected from vinyl chloride resins, polyesters, polyurethanes, ethylene-vinyl acetate copolymer, rubbers, acrylics, and mixtures thereof.

24. The resin composition of claim 22, further comprising stabilizers, fillers, pigments, biocides, carbon black, adhesion promoters, viscosity reducers, thixotropic agents, thickening agents, blowing agents, and mixtures thereof.

25. The resin composition of claim 22, further comprising at least one plasticizer selected from phthalates, adipates, trimellitates, cyclohexanoates, benzoates, and combinations thereof.

26. A plastisol comprising the plasticizer of claim 20.

27. An article comprising the plasticizer of claim 20, the resin composition of claim 22, or the plastisol of claim 26.

28. The article of claim 27, wherein the article is selected from toys, films and sheets, tubing, coated fabrics, wire and cable insulation and jacketing, flooring materials, adhesives, sealants, inks, and medical products.

29. The article of claim 28, made by a process including steps of dryblending and extrusion.

30. The process of claim 1, wherein the ratio of alcohol groups from the polyol to acid groups from the $C_4$ to $C_{10}$ acid in the esterifying step ranges from 1 to 1.1 to 1 to 10 to provide an excess of acid groups to alcohol groups.

31. The process of claim 30, wherein the unreacted input stream includes unreacted $C_4$ to $C_{10}$ acid.

32. The process of claim 30, wherein the reaction byproduct stream includes alkyl triglyceride with a total carbon number of the triester groups less than 20, and triglyceride with a total carbon number of the triester groups greater than 25.

33. The process of claim 30, wherein the reaction rate of the esterifying step is substantially similar to the reaction rate without the recycle of the unreacted $C_4$ to $C_{10}$ acid.

34. The process of claim 1, wherein the ratio of alcohol groups from the polyol to acid groups from the $C_4$ to $C_{10}$ acid in the esterifying step ranges from 1 to 1 to 10 to 1.

35. The process of claim 34, wherein the unreacted input stream includes unreacted polyol.

36. The process of claim 34, wherein the reaction byproduct stream includes monoglyceride, diglyceride, alkyl triglyceride with a total carbon number of the triester groups less than 20, and triglyceride with a total carbon number of the triester groups greater than 25.

37. The process of claim 36, wherein the reaction byproduct stream of the esterifying step also includes olefins, aldehydes, ketones, ethers and combinations thereof.

38. A process for producing a plasticizer comprising:
(i) recovering an aldehyde/alcohol mixture including at least one linear $C_4$ to $C_{10}$ aldehyde, one branched $C_4$ to $C_{10}$ aldehyde, or a combination thereof and at least one linear $C_4$ to $C_{10}$ alcohol, one branched $C_4$ to $C_{10}$ alcohol, or a combination thereof from a hydroformylation process;
(ii) oxidizing the aldehyde/alcohol mixture to form a linear, branched or combination thereof $C_4$ to $C_{10}$ acid;
(iii) esterifying the linear, branched or combination thereof $C_4$ to $C_{10}$ acid with a polyol to yield a linear alkyl triglyceride, a branched alkyl triglyceride or a combination thereof, and reaction byproducts;
(iv) purifying the linear, branched or combination thereof alkyl triglyceride to form a plasticizer stream, a reaction byproduct stream and an unreacted input stream, wherein the total carbon number of the alkyl triester groups ranges from 20 to 25 for greater than or equal to 45 wt % of the plasticizer; and
(v) recycling from the purifying step back to the esterifying step the unreacted input stream and the reaction byproduct stream.

39. The process of claim 38, further including purifying the aldehyde/alcohol mixture of step (i) via distillation before the oxidizing step (ii).

40. The process of claim 38, wherein the at least one branched $C_4$ to $C_{10}$ aldehyde is characterized by a branching of from about 0.8 to about 3.0 branches per molecule.

41. The process of claim 38, wherein the oxidizing step is with oxygen and/or air.

42. The process of claim 38, further including purifying the linear, branched or combination thereof $C_4$ to $C_{10}$ acid of step (ii) from the unreacted aldehyde/alcohol mixture via distillation before the esterifying step (iii).

43. The process of claim 38, wherein said polyol is selected from glycerol, ethylene glycol, and propylene glycol, and mixtures thereof.

44. The process of claim 38, further comprising providing a feed for the e hydroformylation process from dimerization of a feedstock.

45. The process of claim 44, wherein the feedstock comprises an olefin selected from propylene, butenes, pentenes and mixtures thereof.

46. The process of claim 45, wherein the hydroformylation reaction is catalyzed by a metal selected from Groups 8-10 according to the new notation for the Periodic Table as set forth in Chemical Engineering News, 63(5), 27 (1985).

47. The process of claim 46, wherein the hydroformylation reaction is catalyzed by a metal selected from Rh, Co, and mixtures thereof.

48. The process of claim 47, wherein the hydroformylation reaction is catalyzed by a metal selected from Rh, Co, and mixtures thereof including an organic ligand.

49. The process of claim 38, wherein the total carbon number of the triester groups ranges from 20 to 25 for greater than or equal to 75 wt % of the plasticizer.

50. The process of claim 49, wherein the total carbon number of the triester groups ranges from 20 to 25 for greater than or equal to 95 wt % of the plasticizer.

51. The process of claim 38, wherein the oxidizing step is catalyzed.

52. The process of claim 38, wherein the oxidizing step is not catalyzed.

53. The process of claim 38, wherein the esterifying step is catalyzed by at least one metal selected from Ti, Zr or Sn, or a mixture thereof, or catalyzed by an organic acid.

54. The process of claim 38, further comprising dimerizing feedstock selected from propylene, butenes, pentenes and mixtures thereof by solid phosphoric acid or a zeolite dimerization to provide a feed for the hydroformylation process.

55. A plasticizer made by the process of claim 38, wherein the average branching of the alkyl triester groups ranges from about 1.2 to about 3.0 and with the proviso that the plasticizer is substantially free of aryl triglyceride.

56. The plasticizer of claim 55 characterized as being phthalate-free.

57. A resin composition comprising the plasticizer of claim 55 and a resin.

58. The resin composition of claim 57, wherein the resin is selected from vinyl chloride resins, polyesters, polyurethanes, ethylene-vinyl acetate copolymer, rubbers, acrylics, and mixtures thereof.

59. A plastisol comprising the plasticizer of claim 55.

60. An article comprising the plasticizer of claim 55, the resin composition of claim 57, or the plastisol of claim 59.

61. The article of claim 60, wherein the article is selected from toys, films and sheets, tubing, coated fabrics, wire and cable insulation and jacketing, flooring materials, adhesives, sealants, inks, and medical products.

62. The process of claim 38, wherein the ratio of alcohol groups from the polyol to acid groups from the $C_4$ to $C_{10}$ acid in the esterifying step ranges from 1 to 1.1 to 1 to 10 to provide an excess of acid groups to alcohol groups.

63. The process of claim 61, wherein the unreacted input stream includes unreacted $C_4$ to $C_{10}$ acid.

64. The process of claim 61, wherein the reaction byproduct stream includes alkyl triglyceride with a total carbon number of the triester groups less than 20, and triglyceride with a total carbon number of the triester groups greater than 25.

65. The process of claim 61, wherein the reaction rate of the esterifying step is substantially similar to the reaction rate without the recycle of the unreacted $C_4$ to $C_{10}$ acid.

66. The process of claim 38, wherein the ratio of alcohol groups from the polyol to acid groups from the $C_4$ to $C_{10}$ acid in the esterifying step ranges from 1 to 1 to 10 to 1.

67. The process of claim 65, wherein the unreacted input stream includes unreacted polyol.

68. The process of claim 65, wherein the reaction byproduct stream includes monoglyceride, diglyceride, alkyl triglyceride with a total carbon number of the triester groups less than 20, and triglyceride with a total carbon number of the triester groups greater than 25.

69. The process of claim 67, wherein the reaction byproduct stream of the esterifying step also includes olefins, aldehydes, ketones, ethers and combinations thereof.

* * * * *